US012630877B2

(12) United States Patent
Nam

(10) Patent No.: US 12,630,877 B2
(45) Date of Patent: May 19, 2026

(54) SINGLE-STRANDED NUCLEIC ACID FOR REAL-TIME DETECTION OF GENETIC VARIATION OF SINGLE TARGET GENE AND DETECTION METHOD USING THE SAME

(71) Applicant: NURIBIO CO., LTD., Sejong-si (KR)

(72) Inventor: Young Hyean Nam, Suwon-si (KR)

(73) Assignee: NURIBIO CO., LTD., Sejong-si (KR)

( * ) Notice: Subject to any disclaimer, the term of this patent is extended or adjusted under 35 U.S.C. 154(b) by 617 days.

(21) Appl. No.: 16/761,244

(22) PCT Filed: Apr. 10, 2020

(86) PCT No.: PCT/KR2020/004946
§ 371 (c)(1),
(2) Date: May 2, 2020

(87) PCT Pub. No.: WO2021/172653
PCT Pub. Date: Sep. 2, 2021

(65) Prior Publication Data
US 2022/0119882 A1 Apr. 21, 2022

(30) Foreign Application Priority Data
Feb. 28, 2020 (KR) .................... 10-2020-000024728

(51) Int. Cl.
| | |
|---|---|
| *C12Q 1/68* | (2018.01) |
| *C12N 9/22* | (2006.01) |
| *C12Q 1/6818* | (2018.01) |
| *C12Q 1/6851* | (2018.01) |
| *C12Q 1/6853* | (2018.01) |
| *C12Q 1/6876* | (2018.01) |

(52) U.S. Cl.
CPC ............. *C12Q 1/6876* (2013.01); *C12N 9/22* (2013.01); *C12Q 1/6818* (2013.01); *C12Q 1/6851* (2013.01); *C12Q 1/6853* (2013.01); *C12Q 2521/327* (2013.01); *C12Q 2525/121* (2013.01); *C12Q 2525/131* (2013.01); *C12Q 2525/161* (2013.01); *C12Q 2525/185* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,763,181 A | 6/1998 | Han et al. | |
| 2003/0129589 A1* | 7/2003 | Koster | .................. C07F 9/2408 |
| | | | 422/68.1 |
| 2006/0210983 A1* | 9/2006 | Usui | ...................... C12Q 1/682 |
| | | | 435/6.11 |
| 2011/0014613 A1* | 1/2011 | Pfuetzner-Riehn | ......................... |
| | | | C12Q 1/6883 |
| | | | 435/6.14 |
| 2011/0151467 A1* | 6/2011 | Usui | .................... C12Q 1/6848 |
| | | | 435/6.12 |
| 2011/0294674 A1 | 12/2011 | Cheung et al. | |

FOREIGN PATENT DOCUMENTS

KR    1020170095752 A    8/2017

OTHER PUBLICATIONS

Marotti et al. Nucleotide sequence of the cynomolgus monkey apolipoprotein E cDNA. Nucleic Acids Research, vol. 17(4), p. 1778, 1989.*
Lowe, T., et al. A computer program for selection of oligonucleotide primers for polymerase chain reactions. Nucleic Acids Research, vol. 18(7), p. 1757-1761, 1990.*
Tagalakis, AD., et al. Correction of the neuropathogenic human apolipoprotein E4 (APOE4) gene to APOE3 in vitro using synthetic RNA/DNA oligonucleotides (chimeraplasts). Jornal of Molecular Neuroscience, vol. 25, p. 95-103, (2005).*
Harvey et al., Characterization and applications of CataCleave probe in real-time detection assays, Analytical Biochemistry, 2004, pp. 246-255, vol. 333.
Kandimalla et al., 'Cyclicons' as Hybridization-Based Fluorescent Primer-Probes: Synthesis, Properties and Application in Real-Time PCR, 2000, Bioorganic & Medicinal Chemistry, pp. 1911-1916, vol. 8.
Harvey et al., SNP Analysis Using CataCleave Probes, Journal of Clinical Laboratory Analysis, 2008, pp. 192-203, vol. 22.

* cited by examiner

*Primary Examiner* — Suryaprabha Chunduru
(74) *Attorney, Agent, or Firm* — LEX IP MEISTER, PLLC

(57) ABSTRACT

The present disclosure relates to a single nucleic acid for real-time detection for single nucleotide polymorphism (SNP) analysis of apolipoprotein E (ApoE) gene and a detection method using the same.

3 Claims, 21 Drawing Sheets

Specification includes a Sequence Listing.

Amplification Plot

FIG. 7

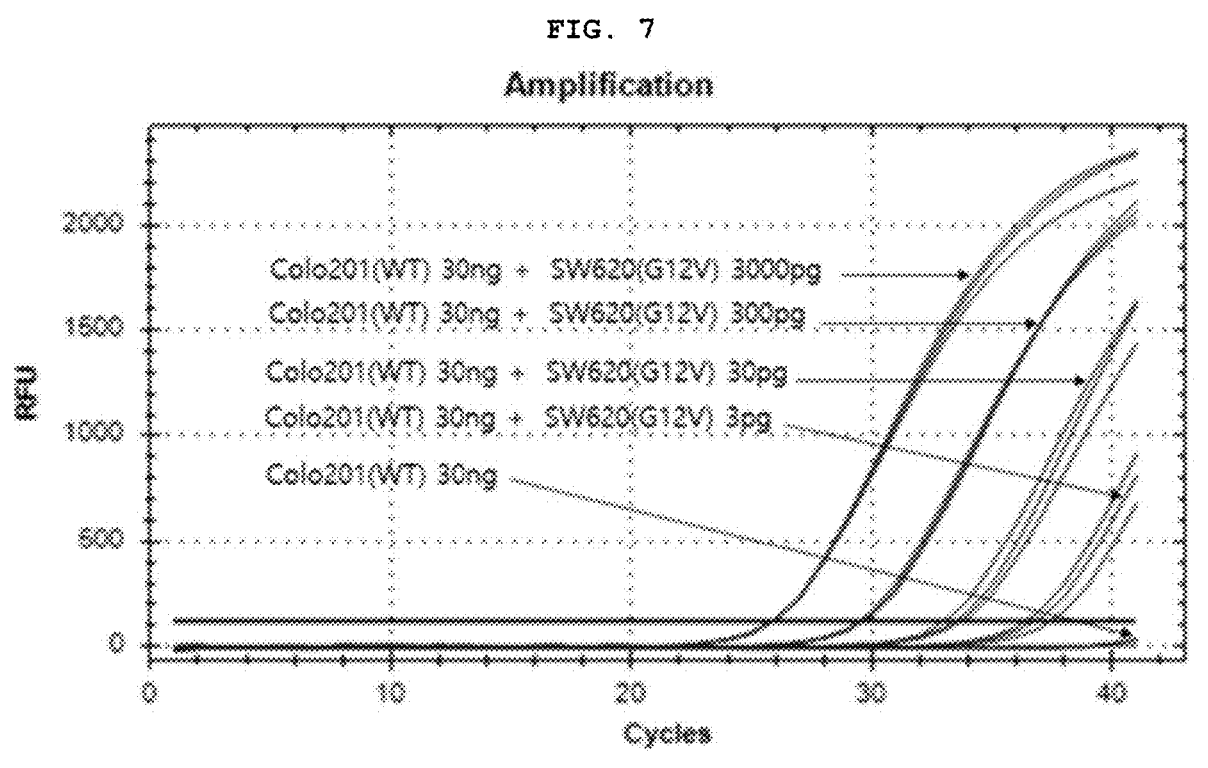

Amplification

Colo201(WT) 30ng + SW620(G12V) 3000pg
Colo201(WT) 30ng + SW620(G12V) 300pg
Colo201(WT) 30ng + SW620(G12V) 30pg
Colo201(WT) 30ng + SW620(G12V) 3pg
Colo201(WT) 30ng Cycles

FIG. 8

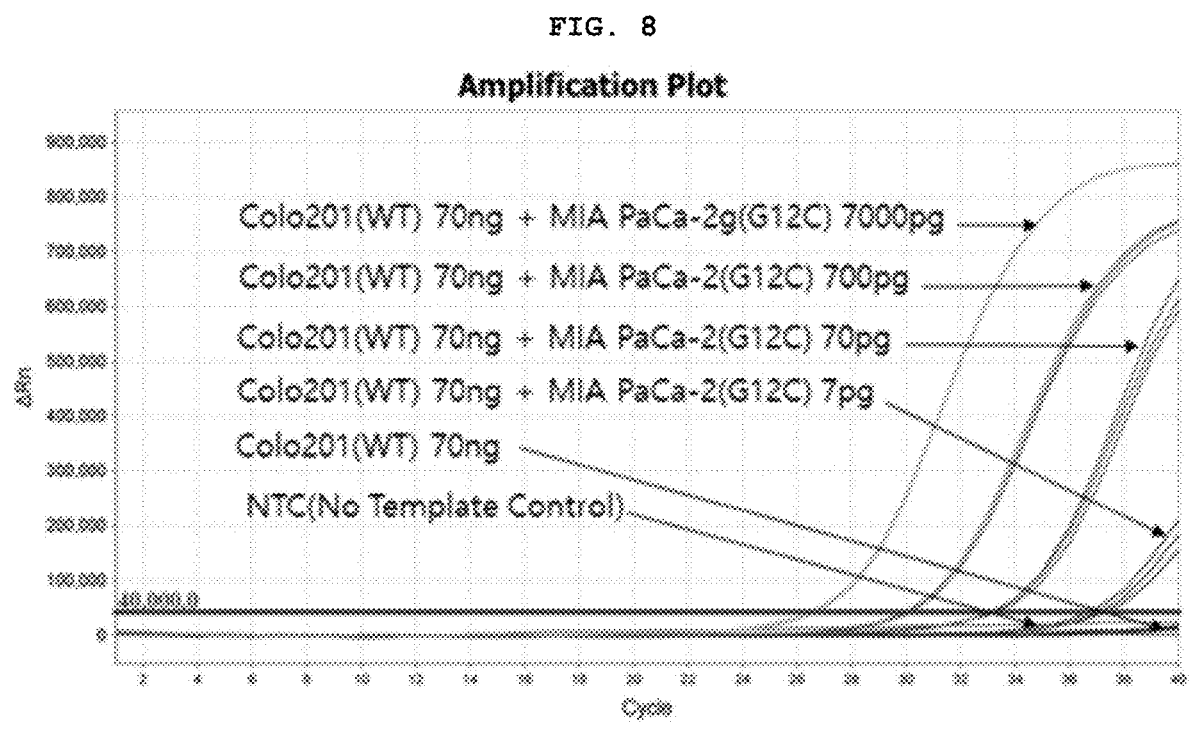

Amplification Plot

Colo201(WT) 70ng + MIA PaCa-2g(G12C) 7000pg

Colo201(WT) 70ng + MIA PaCa-2(G12C) 700pg

Colo201(WT) 70ng + MIA PaCa-2(G12C) 70pg

Colo201(WT) 70ng + MIA PaCa-2(G12C) 7pg

Colo201(WT) 70ng

NTC(No Template Control)

FIG. 9

Amplification

FIG. 11

SEQUENCE LISTING

<160> NUMBER OF SEQ ID NOS: 40

<210> SEQ ID NO 1
<211> LENGTH: 21
<212> TYPE: DNA

-continued

```
<213> ORGANISM: Artificial Sequence
<220> FEATURE:
<223> OTHER INFORMATION: Forward primer for detecting ApoE gene

<400> SEQUENCE: 1
gaaggcctac aaatcggaac t                                             21

<210> SEQ ID NO 2
<211> LENGTH: 17
<212> TYPE: DNA
<213> ORGANISM: Artificial Sequence
<220> FEATURE:
<223> OTHER INFORMATION: Reverse primer for detecting ApoE gene

<400> SEQUENCE: 2
gccacctgct ccttcac                                                  17

<210> SEQ ID NO 3
<211> LENGTH: 16
<212> TYPE: DNA
<213> ORGANISM: Artificial Sequence
<220> FEATURE:
<223> OTHER INFORMATION: Single Nucleic Acid for detecting ApoE gene
<220> FEATURE:
<223> OTHER INFORMATION: RNA is located in 10th of sequence

<400> SEQUENCE: 3
gaggacgtgu gcggcc                                                   16

<210> SEQ ID NO 4
<211> LENGTH: 16
<212> TYPE: DNA
<213> ORGANISM: Artificial Sequence
<220> FEATURE:
<223> OTHER INFORMATION: Single Nucleic Acid for detecting ApoE gene
<220> FEATURE:
<223> OTHER INFORMATION: RNA is located in 10th of sequence.

<400> SEQUENCE: 4
gaggacgtgc gcggcc                                                   16

<210> SEQ ID NO 5
<211> LENGTH: 18
<212> TYPE: DNA
<213> ORGANISM: Artificial Sequence
<220> FEATURE:
<223> OTHER INFORMATION: Single Nucleic Acid for detecting ApoE gene
<220> FEATURE:
<223> OTHER INFORMATION: RNA is located in 10th of sequence.

<400> SEQUENCE: 5
ctgcagaagu gcctggca                                                 18

<210> SEQ ID NO 6
<211> LENGTH: 16
<212> TYPE: DNA
<213> ORGANISM: Artificial Sequence
<220> FEATURE:
<223> OTHER INFORMATION: Single Nucleic Acid for detecting ApoE gene
<220> FEATURE:
<223> OTHER INFORMATION: RNA is located in 8th of sequence.

<400> SEQUENCE: 6
gcagaagcgc ctggca                                                   16

<210> SEQ ID NO 7
<211> LENGTH: 16
```

-continued

```
<212> TYPE: DNA
<213> ORGANISM: Artificial Sequence
<220> FEATURE:
<223> OTHER INFORMATION: Single Nucleic Acid for detecting G13D mutation
      of KRAS gene
<220> FEATURE:
<223> OTHER INFORMATION: RNA is located in 9th of sequence.

<400> SEQUENCE: 7
agctggtgac gtaggc                                                          16

<210> SEQ ID NO 8
<211> LENGTH: 16
<212> TYPE: DNA
<213> ORGANISM: Artificial Sequence
<220> FEATURE:
<223> OTHER INFORMATION: Single Nucleic Acid for detecting wild type of
      KRAS gene
<220> FEATURE:
<223> OTHER INFORMATION: RNA is located in 9th of sequence.

<400> SEQUENCE: 8
agctggtggc gtaggc                                                          16

<210> SEQ ID NO 9
<211> LENGTH: 27
<212> TYPE: DNA
<213> ORGANISM: Artificial Sequence
<220> FEATURE:
<223> OTHER INFORMATION: Forward primer for detecting G13D mutation of
      KRAS gene

<400> SEQUENCE: 9
cctgctgaaa atgactgaat ataaact                                              27

<210> SEQ ID NO 10
<211> LENGTH: 26
<212> TYPE: DNA
<213> ORGANISM: Artificial Sequence
<220> FEATURE:
<223> OTHER INFORMATION: Reverse primer for detecting G13D mutation of
      KRAS gene

<400> SEQUENCE: 10
tcgtccacaa aatgattctg aattag                                               26

<210> SEQ ID NO 11
<211> LENGTH: 20
<212> TYPE: DNA
<213> ORGANISM: Artificial Sequence
<220> FEATURE:
<223> OTHER INFORMATION: Single nucleic acid for detecting ApoE gene
<220> FEATURE:
<223> OTHER INFORMATION: RNA is located in 18th of sequence.

<400> SEQUENCE: 11
cggtcatgga ggacgtgugc                                                      20

<210> SEQ ID NO 12
<211> LENGTH: 20
<212> TYPE: DNA
<213> ORGANISM: Artificial Sequence
<220> FEATURE:
<223> OTHER INFORMATION: Single nucleic acid for detecting ApoE gene
<220> FEATURE:
<223> OTHER INFORMATION: RNA is located in 18th of sequence.

<400> SEQUENCE: 12
```

-continued

```
gcggatatgg aggacgtgcg                                              20

<210> SEQ ID NO 13
<211> LENGTH: 21
<212> TYPE: DNA
<213> ORGANISM: Artificial Sequence
<220> FEATURE:
<223> OTHER INFORMATION: Single nucleic acid for detecting ApoE gene
<220> FEATURE:
<223> OTHER INFORMATION: RNA is located in 19th of sequence.

<400> SEQUENCE: 13
ctggtacact gccaggcact t                                            21

<210> SEQ ID NO 14
<211> LENGTH: 22
<212> TYPE: DNA
<213> ORGANISM: Artificial Sequence
<220> FEATURE:
<223> OTHER INFORMATION: Single nucleic acid for detecting ApoE gene
<220> FEATURE:
<223> OTHER INFORMATION: RNA is located in 18th of sequence.

<400> SEQUENCE: 14
ctggtacact gccaggcgat tc                                           22

<210> SEQ ID NO 15
<211> LENGTH: 23
<212> TYPE: DNA
<213> ORGANISM: Artificial Sequence
<220> FEATURE:
<223> OTHER INFORMATION: Single nucleic acid for detecting codon
      mutation of KRAS gene
<220> FEATURE:
<223> OTHER INFORMATION: RNA is located in 21th of sequence

<400> SEQUENCE: 15
acttgtggta gttggagctg utg                                          23

<210> SEQ ID NO 16
<211> LENGTH: 23
<212> TYPE: DNA
<213> ORGANISM: Artificial Sequence
<220> FEATURE:
<223> OTHER INFORMATION: Single nucleic acid for detecting codon
      mutation of KRAS gene
<220> FEATURE:
<223> OTHER INFORMATION: RNA is located in 21th of sequence.

<400> SEQUENCE: 16
aacttgtggt agttggagct ugt                                          23

<210> SEQ ID NO 17
<211> LENGTH: 23
<212> TYPE: DNA
<213> ORGANISM: Artificial Sequence
<220> FEATURE:
<223> OTHER INFORMATION: Single nucleic acid for detecting codon
      mutation of KRAS gene
<220> FEATURE:
<223> OTHER INFORMATION: RNA is located in 21th of sequence.

<400> SEQUENCE: 17
aacttgtggt agttggagct agt                                          23

<210> SEQ ID NO 18
<211> LENGTH: 25
<212> TYPE: DNA
```

-continued

```
<213> ORGANISM: Artificial Sequence
<220> FEATURE:
<223> OTHER INFORMATION: Reverse primer for detecting codon mutation of
      KRAS gene

<400> SEQUENCE: 18
catattcgtc cacaaaatga ttctg                                        25

<210> SEQ ID NO 19
<211> LENGTH: 18
<212> TYPE: DNA
<213> ORGANISM: Artificial Sequence
<220> FEATURE:
<223> OTHER INFORMATION: Single nucleic acid for detecting mutation of
      EGFR gene
<220> FEATURE:
<223> OTHER INFORMATION: RNA is located in 16th of sequence.

<400> SEQUENCE: 19
ccgtgcagct catcaugc                                                18

<210> SEQ ID NO 20
<211> LENGTH: 25
<212> TYPE: DNA
<213> ORGANISM: Artificial Sequence
<220> FEATURE:
<223> OTHER INFORMATION: Reverse primer for detecting mutation of EGFR
      gene

<400> SEQUENCE: 20
ccttgtgtta aggacatag tccag                                         25

<210> SEQ ID NO 21
<211> LENGTH: 24
<212> TYPE: DNA
<213> ORGANISM: Artificial Sequence
<220> FEATURE:
<223> OTHER INFORMATION: Single nucleic acid for detecting isoform of
      let-7a gene
<220> FEATURE:
<223> OTHER INFORMATION: RNA is located in 22th of sequence.

<400> SEQUENCE: 21
gctgcttgag gtagtaggtt guat                                         24

<210> SEQ ID NO 22
<211> LENGTH: 18
<212> TYPE: DNA
<213> ORGANISM: Artificial Sequence
<220> FEATURE:
<223> OTHER INFORMATION: Reverse primer for detecting isoform of let-7a
      gene

<400> SEQUENCE: 22
gccgctgagg tagtaggt                                                18

<210> SEQ ID NO 23
<211> LENGTH: 28
<212> TYPE: DNA
<213> ORGANISM: Artificial Sequence
<220> FEATURE:
<223> OTHER INFORMATION: RT primer for detecting isoform of let-7a gene

<400> SEQUENCE: 23
gctaacgtct gtacttcgtc atttaact                                     28

<210> SEQ ID NO 24
```

-continued

```
<211> LENGTH: 24
<212> TYPE: DNA
<213> ORGANISM: Artificial Sequence
<220> FEATURE:
<223> OTHER INFORMATION: Single nucleic acid for detecting isoform of
      let-7d gene
<220> FEATURE:
<223> OTHER INFORMATION: RNA is located in 22th of sequence.

<400> SEQUENCE: 24
gctgctagag gtagtaggtt gcat                                               24

<210> SEQ ID NO 25
<211> LENGTH: 18
<212> TYPE: DNA
<213> ORGANISM: Artificial Sequence
<220> FEATURE:
<223> OTHER INFORMATION: Reverse primer for detecting isoform of let-7d
      gene

<400> SEQUENCE: 25
gccgctgagg tagtaggt                                                      18

<210> SEQ ID NO 26
<211> LENGTH: 28
<212> TYPE: DNA
<213> ORGANISM: Artificial Sequence
<220> FEATURE:
<223> OTHER INFORMATION: RT primer for detecting isoform of let-7d gene

<400> SEQUENCE: 26
gctaacgtct gtacttcgtc atttaact                                          28

<210> SEQ ID NO 27
<211> LENGTH: 21
<212> TYPE: DNA
<213> ORGANISM: Artificial Sequence
<220> FEATURE:
<223> OTHER INFORMATION: Single nucleic acid for detecting isoform of
      miRNA 34a gene
<220> FEATURE:
<223> OTHER INFORMATION: RNA is located in 19th of sequence

<400> SEQUENCE: 27
ttggcagtgt cttagctggt t                                                 21

<210> SEQ ID NO 28
<211> LENGTH: 26
<212> TYPE: DNA
<213> ORGANISM: Artificial Sequence
<220> FEATURE:
<223> OTHER INFORMATION: Reverse primer for detecting isoform of miRNA
      34a gene

<400> SEQUENCE: 28
gtctcgacgt tctttttttt ttttac                                            26

<210> SEQ ID NO 29
<211> LENGTH: 26
<212> TYPE: DNA
<213> ORGANISM: Artificial Sequence
<220> FEATURE:
<223> OTHER INFORMATION: RT primer for detecting isoform of miRNA 34a
      gene

<400> SEQUENCE: 29
gtctcgacgt tctttttttt ttttac                                            26
```

```
<210> SEQ ID NO 30
<211> LENGTH: 25
<212> TYPE: DNA
<213> ORGANISM: Artificial Sequence
<220> FEATURE:
<223> OTHER INFORMATION: Single nucleic acid for detecting isoform of
      miRNA 34b gene
<220> FEATURE:
<223> OTHER INFORMATION: RNA is located in 23th of sequence

<400> SEQUENCE: 30
gtctaggcag tgtcattagc tgatt                                          25

<210> SEQ ID NO 31
<211> LENGTH: 25
<212> TYPE: DNA
<213> ORGANISM: Artificial Sequence
<220> FEATURE:
<223> OTHER INFORMATION: Reverse primer for detecting isoform of miRNA
      34b gene

<400> SEQUENCE: 31
gtctcgacgt tctttttttt ttttc                                          25

<210> SEQ ID NO 32
<211> LENGTH: 25
<212> TYPE: DNA
<213> ORGANISM: Artificial Sequence
<220> FEATURE:
<223> OTHER INFORMATION: RT primer for detecting isoform of miRNA 34b
      gene

<400> SEQUENCE: 32
gtctcgacgt tctttttttt ttttc                                          25

<210> SEQ ID NO 33
<211> LENGTH: 23
<212> TYPE: DNA
<213> ORGANISM: Artificial Sequence
<220> FEATURE:
<223> OTHER INFORMATION: Single nucleic acid for detecting isoform of
      miRNA 34c gene
<220> FEATURE:
<223> OTHER INFORMATION: RNA is located in 21th of sequence

<400> SEQUENCE: 33
ccaggcagtg tagttagctg att                                            23

<210> SEQ ID NO 34
<211> LENGTH: 26
<212> TYPE: DNA
<213> ORGANISM: Artificial Sequence
<220> FEATURE:
<223> OTHER INFORMATION: Reverse primer for detecting isoform of miRNA
      34c gene

<400> SEQUENCE: 34
gtctcgacgt tctttttttt ttttgc                                         26

<210> SEQ ID NO 35
<211> LENGTH: 26
<212> TYPE: DNA
<213> ORGANISM: Artificial Sequence
<220> FEATURE:
<223> OTHER INFORMATION: RT primer for detecting isoform of miRNA 34c
      gene

<400> SEQUENCE: 35
```

-continued

```
gtctcgacgt tctttttttt ttttgc                                  26

<210> SEQ ID NO 36
<211> LENGTH: 22
<212> TYPE: DNA
<213> ORGANISM: Artificial Sequence
<220> FEATURE:
<223> OTHER INFORMATION: Single nucleic acid for detecting mutation of
      KRAS gene
<220> FEATURE:
<223> OTHER INFORMATION: RNA is located in 20th of sequence.

<400> SEQUENCE: 36
cttgtggtag ttggagctga tg                                      22

<210> SEQ ID NO 37
<211> LENGTH: 21
<212> TYPE: DNA
<213> ORGANISM: Artificial Sequence
<220> FEATURE:
<223> OTHER INFORMATION: Single nucleic acid for detecting mutation of
      KRAS gene
<220> FEATURE:
<223> OTHER INFORMATION: RNA is located in 19th of sequence.

<400> SEQUENCE: 37
cttgtggtag ttggagctga t                                       21

<210> SEQ ID NO 38
<211> LENGTH: 23
<212> TYPE: DNA
<213> ORGANISM: Artificial Sequence
<220> FEATURE:
<223> OTHER INFORMATION: Single nucleic acid for detecting mutation of
      KRAS gene
<220> FEATURE:
<223> OTHER INFORMATION: RNA is located in 21th of sequence.

<400> SEQUENCE: 38
cttgtggtag ttggagctga tgg                                     23

<210> SEQ ID NO 39
<211> LENGTH: 22
<212> TYPE: RNA
<213> ORGANISM: Artificial Sequence
<220> FEATURE:
<223> OTHER INFORMATION: let-7a miRNA

<400> SEQUENCE: 39
ugagguagua gguuguauag uu                                      22

<210> SEQ ID NO 40
<211> LENGTH: 22
<212> TYPE: RNA
<213> ORGANISM: Artificial Sequence
<220> FEATURE:
<223> OTHER INFORMATION: let-7d miRNA

<400> SEQUENCE: 40
agagguagua gguugcauag uu                                      22
```

SINGLE-STRANDED NUCLEIC ACID FOR REAL-TIME DETECTION OF GENETIC VARIATION OF SINGLE TARGET GENE AND DETECTION METHOD USING THE SAME

CROSS-REFERENCE TO RELATED APPLICATION

This application is a 371 U.S. national stage of PCT/KR2020/004946, filed Apr. 10, 2020, which claims the benefit of Korean Patent Application No. KR 10-2020-000024728 filed Feb. 28, 2020, and the contents of which are incorporated herein by reference.

TECHNICAL FIELD

The present invention relates to a single-stranded nucleic acid for real-time detection of the genetic variation of a single target gene and a detection method using the same, and more particularly to a real-time detection method for the genetic variation of a single target gene and a kit for the same, where the real-time detection method uses a single-stranded nucleic acid having a structure of X-Y-Z and comprising a nucleotide sequence that can form a complementary bond to all or part of the nucleotide sequence of a single target gene containing a genetic variation such as single nucleotide polymorphism (SNP), point mutation, or miRNA isoform.

BACKGROUND ART

Single nucleotide polymorphisms (SNPs), the most common type of variation in the genome, have proven to play a role in the development of different diseases (Barreiro L B, et al., *Methods Mol. Biol.*, 578:255-276, 2009; Beaudet L. et al., *Genome Res.*, 11(4):600-608, 2001). Diagnostic methods using detection of SNPs are therefore a very efficient and fast way to diagnose different diseases associated with genetic variations in an early stage. There have been developed numerous methods for accurate detection of SNPs, and further researches are being carried out in association with the SNP detection methods (Ermini M L. et al., *Biosen. & Bioele.*, 61:28-37, 2014; K. Chang et al., *Biosen. & Bioele.*, 66:297-307, 2015).

The most widely used methods for multiple genetic analyses are: a conventional PCR (Polymerase Chain Reaction) assay and a multiplex PCR assay.

The conventional PCR uses a DNA template and arbitrarily designed primers or probes hybridized with a fluorescent substance and a quencher, allowing for precise amplification of a specific region of the DNA target to be detected. A single DNA target is amplified with a single reaction, and on account of this it requires a daunting task of repeating the same procedures for multiple target DNAs to be amplified.

The multiplex PCR makes it possible to perform concurrent amplification and analysis of different DNA targets with multiple polymerase chain reactions in a single tube. Yet, multiple primers or probes are used in a single tube at the same time, which possibly causes a cross reaction of the primer or primers and thus limits the number of the DNA targets to be amplified at once. Further, lots of work and time is required in determining the conditions for the reactions, but resulting in poor outcomes in the aspects of sensitivity and specificity (Hardenbol P. et al., *Nat. Biotechnol.*, 21(6): 673-678, 2003).

In recent years, many researches have been devoted to the high-throughput analytical techniques that involve concurrent amplification of different DNA targets using universal primers instead of multiple polymerase chain reactions. The techniques may include, for example, SNPlex designed for simultaneous analysis of SNPs in different DNA targets, Goldengate assay, molecular inversion probes (MIPs), etc.

SNPlex is an analytical technique that involves the steps of oligonucleotide ligation assay (OLA); purification using exonuclease; PCR amplification with universal primer sequences on both sides of the probe; and analysis of the amplified PCR products on a DNA chip using the ZipCode sequence contained in the probe (Tobler et al., *J. Biomol. Tech.*, 16(4):398-406, 2005).

Goldengate assay is an analytical technique that includes allele-specific primer extension of a genomic DNA mobilized on a solid surface with an upstream probe; ligation reaction of the DNA with a downstream probe; washing away probes not ligated to the DNA; amplification with universal primer sequences contained in the probe as in SNPlex; and analysis of the amplified PCR products on an Illumina BeadChip (Shen R. et al., *Mutat. Res.*, 573(1-2): 70-82, 2005).

Molecular inversion probe (MIP) assay is an analytical technique that includes carrying out a gap-ligation using padlock probes; using an exonuclease to remove probes and genomic DNA without DNA links; linearizing the padlock probes using an uracil-N-glycosylase; activating a PCR reaction using an universal primer sequence contained in the probes; and forming hybridization of the PCR product with a GenFlex Tag Array (Affymetrix) to analyze single nucleotide polymorphisms (SNPs) (Hardenbol P. et al., *Nat. Biotechnol.*, 21(6):673-678, 2003).

These approaches, however, involves transferring a part of the reaction products from a first tube to a second tube or uses different enzymes, possibly causing cross-contamination between the different samples and making the experimental procedures complicated. The single nucleotide polymorphisms (SNPs) are detectable as many as the probes with fluorescent markers; accordingly, with more SNPs to analyze, the higher the analysis costs.

Generally, point mutations take place during DNA replication. DNA replication occurs when two single strands of DNA are produced from one double-stranded DNA. Each of the single strands of DNA acts as a template for the synthesis of the complementary strand. A single point mutation can make a change in the whole DNA sequence. Changing one purine or pyrimidine may lead to a change in the amino acid that the nucleotides code for.

Point mutations may arise from spontaneous mutations occurring during DNA replication, and the rate of mutation may be increased by such a cause of the mutation.

In 1959, Ernst Freese coined the terms "transitions" or "transversions" to categorize different types of point mutations. Transitions are a point mutation that changes a purine nucleotide to another purine, or a pyrimidine nucleotide to another pyrimidine. Transversions are a point mutation that replaces a purine with a pyrimidine or vice versa. There is a difference in the rate of mutation for transition (Alpha) and transversion (Beta). Transitions are about ten times more common than transversions.

As known to those skilled in the art, point mutations are classified into three functional categories: nonsense mutations including stop-gain and stop-loss that cause the protein abnormally shortened or extended; missense mutations coding a different amino acid (the mutation changing a valine to glutamic acid in the BRAF gene may lead to activation of the RAF protein causing unlimited proliferation signaling in cancer cells); and silent mutations coding for the same amino acid.

Point mutations are known to cause specific diseases, such as cancer associated with a point mutation in multiple tumor suppressor; neurofibromatosis caused by a point mutation in Neurofibromin 1 or 2 gene; sickle-cell anemia resulting from a point mutation in the β-globin chain of hemoglobin, which causes the hydrophilic amino acid glutamic acid to be replaced with the hydrophobic amino acid valine at the sixth position; Tay-Sachs disease; or color blindness.

The diagnosis of point mutations plays an important role especially in making a diagnosis and selecting therapeutic drugs of the cancers. Companion diagnostics are used to aid in selecting or excluding specific therapeutic drugs for cancerous mutations. The development of anticancer drugs targeting a specific mutation has recently been on a rising trend.

The diagnostic methods for those mutations are conducted using PCR, NGS, ddPCR, etc. As the liquid biopsy becomes more important and draws more interest, the measurement methods require the higher precision. But the conventional measurement methods guarantee no capability for analysis high enough and need high-cost equipment and complicated analytic procedures when they have high capability for analysis. For this reason, there is a demand for developing measurement methods applicable with simple analytical procedures.

The inventors of the present invention have long been making researches on the diagnostic methods for cancers with precision simply by raising sensitivity and specificity, which are inherently low in the real-time detection of genetic variations, such as SNP, point mutation, miRNA isoform, etc., and have found the fact that the use of a single-stranded nucleic acid increases sensitivity and specificity and hence can be very helpful in the diagnosis of various diseases like cancers associated with genetic variations, thereby completing the present invention.

DISCLOSURE OF INVENTION

Technical Problem

It is an object of the present invention to provide a single-stranded nucleic acid for detection of a genetic variation of a single target gene, which single-stranded nucleic acid has: (i) a structure of X-Y-Z; (ii) a complementary bonding to all or part of the nucleotide sequence of a single target gene containing a genetic variation; and (iii) at least two identical or different detectable markers attached to both ends or the inside thereof. The Y region is an RNA having a genetic sequence of one or two nucleotides at a locus of the single target gene.

It is another object of the present invention to provide a single-stranded nucleic acid for detection of a genetic variation of a single target gene, where when the genetic variation of the single target gene is single nucleotide polymorphism (SNP), then the single-stranded nucleic acid has: (a) the X region being a DNA having a genetic sequence of 4 to 20 nucleotides; and (b) the Z region being a DNA having a genetic sequence of 4 to 20 nucleotides.

It is still another object of the present invention to provide a single-stranded nucleic acid for detection of a genetic variation of a single target gene, where when the genetic variation of the single target gene is single nucleotide polymorphism (SNP), point mutation, or miRNA isoform, then the single-stranded nucleic acid has: (c) the X region being a DNA having a genetic sequence of 10 to 30 nucleotides, and (d) the Z region being a DNA having a genetic sequence of 1 to 5 nucleotides.

It is further another object of the present invention to provide a real-time detection kit for genetic variation of a single target gene that includes the single-stranded nucleic acid.

It is still further another object of the present invention to provide a detection method for genetic variation of a single target gene that includes: (a) obtaining a target nucleic acid containing a genetic variation to be detected from a biological sample; (b) preparing the single-stranded nucleic acid for detection of genetic variation of a single target gene; (c) mixing the target nucleic acid obtained in step (a) and the single-stranded nucleic acid prepared in step (b) with a primer set having a nucleotide sequence complementary to the nucleotide sequence of the target nucleic acid of step (a) and a cleavage reagent, and then amplifying a complex of the target nucleic acid containing the genetic variation and the single-stranded nucleic acid through an extension reaction; and (d) determining the quantity of fragments of the single-stranded nucleic acid separated from the complex of the target nucleic acid containing the genetic variation and the single-stranded nucleic acid amplified in step (c).

Technical Solution

To achieve the objects of the present invention, there is provided a single-stranded nucleic acid for detection of a genetic variation of a single target gene.

More specifically, the single-stranded nucleic acid may include: (i) a structure of X-Y-Z; (ii) a complementary bonding to all or part of the nucleotide sequence of a single target gene containing a genetic variation; and (iii) at least two identical or different detectable markers attached to both ends or the inside thereof. The Y region is an RNA having a genetic sequence of one or two nucleotides at a locus of the single target gene, and is cut out by a cleavage reagent when hybridized with the single target gene.

When the genetic variation of the single target gene is single nucleotide polymorphism (SNP), then the single-stranded nucleic acid may have: (a) the X region being a DNA having a genetic sequence of 4 to 20 nucleotides; and (b) the Z region being a DNA having a genetic sequence of 4 to 20 nucleotides. When the genetic variation of the single target gene is single nucleotide polymorphism (SNP), point mutation, or miRNA isoform, then the single-stranded nucleic acid may have: (c) the X region being a DNA having a genetic sequence of 10 to 30 nucleotides, and (d) the Z region being a DNA having a genetic sequence of 1 to 5 nucleotides.

When the genetic variation of the single target gene is single nucleotide polymorphism (SNP), then both the X and the Z regions are separated from the single target gene as the Y region is cut out by a cleavage reagent following hybridization of the single target gene and the single-stranded nucleic acid, allowing the single-stranded nucleic acid to act as a probe. Alternatively, when the genetic variation of the single target gene is single nucleotide polymorphism (SNP), point mutation, or miRNA isoform, then the Z region other than the X region is separated from the single target gene as the Y region is cut out by a cleavage reagent following hybridization of the single target gene and the single-stranded nucleic acid, allowing the single-stranded nucleic acid to act as a primer and a probe at once.

In another aspect of the present invention, there is provided a real-time detection kit for genetic variation of a single target gene that includes the single-stranded nucleic acid.

In further another aspect of the present invention, there is provided a detection method for genetic variation of a single target gene that includes: (a) obtaining a target nucleic acid containing a genetic variation to be detected from a biological sample; (b) preparing the single-stranded nucleic acid for detection of genetic variation of a single target gene; (c) mixing the target nucleic acid obtained in step (a) and the single-stranded nucleic acid prepared in step (b) with a primer set having a nucleotide sequence complementary to the nucleotide sequence of the target nucleic acid of step (a) and a cleavage reagent, and then amplifying a complex of the target nucleic acid containing the genetic variation and the single-stranded nucleic acid through an extension reaction; and (d) determining the quantity of fragments of the single-stranded nucleic acid separated from the complex of the target nucleic acid containing the genetic variation and the single-stranded nucleic acid amplified in step (c).

Effects of Invention

Compared to the conventional analytic method for SNP and point mutation using qPCR, the real-time detection method for a genetic variation of a single target gene using a single-stranded nucleic acid according to the present invention has no need of using a separate probe at a specific locus for real-time identification of the variation and thus allows for more precise measurements of the genetic variation such as SNP and point mutation. In other words, because the single-stranded nucleic acid of the present invention is cut out only with a cleavage reagent, the detection method can achieve measurements with higher precision than the conventional probe-mediated methods for detection of genetic variation.

Further, the analysis of genetic variation such as SNP and point mutation using a single-stranded nucleic acid according to the present invention facilitates instantaneous discrimination of mutations without a separate mutant identification process like the melting temperature analysis.

Accordingly, the single-stranded nucleic acid and the real-time detection method for detecting the genetic variation of a single target gene using the single-stranded nucleic acid according to the present invention allow for fast and precise discrimination of different point mutations in KRAS, EGFR, etc. and thus can be favorably applied to the diagnosis, selection of therapeutic drugs, and accurate prognosis for different diseases including cancers.

6 stranded nucleic acid type 1 (SEQ ID NO: 7) to measure the genetic expression of G13D mutant on the function of the gDNA concentration.

Figure 3:
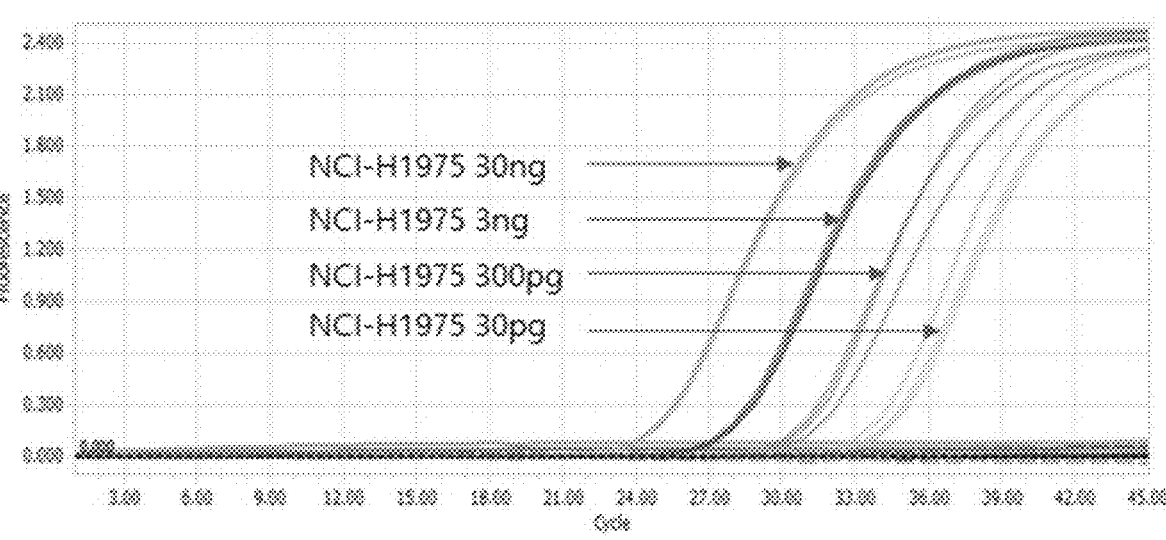

FIG. 3 is a presentation of PCR results measuring the genetic expression of wild-type KRAS using a KRAS wild-type single-stranded nucleic acid according to another embodiment of the present invention. Genomic DNA (gDNA) from KRAS wild-type NCI-H1975 cell-line was diluted by concentrations, and PCR was carried out using a KRAS wild-type single-stranded nucleic acid type 1 (SEQ ID NO: 8) to measure the genetic expression of wild-type KRAS on the function of the gDNA concentration.

Figure 4:
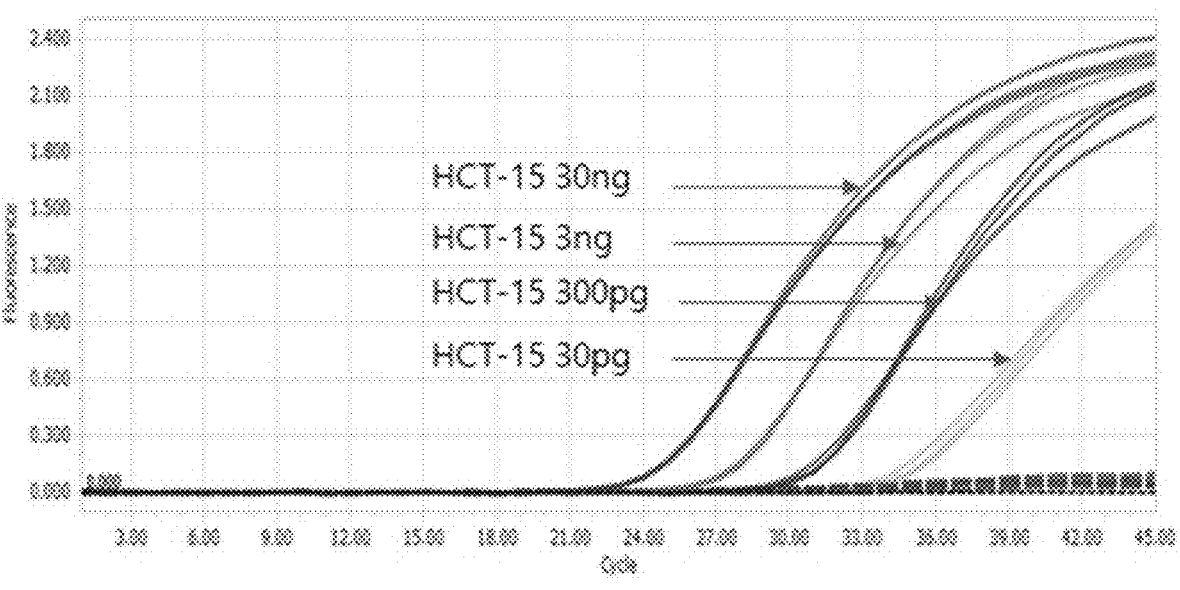

FIG. 4 is a presentation of PCR results measuring the genetic expression of wild-type KRAS using a KRAS wild-type single-stranded nucleic acid type 1 according to another embodiment of the present invention. Genomic DNA (gDNA) from HCT-15 cell-line was diluted by concentrations, and PCR was carried out using a KRAS wild-type single-stranded nucleic acid type 1 (SEQ ID NO: 8) to measure the genetic expression of wild-type KRAS on the function of the gDNA concentration. According to the PCR results, the HCT-15 cell-line, a heterozygous gene, contained both the G13D mutant and the KRAS wild-type gene.

Figure 5:
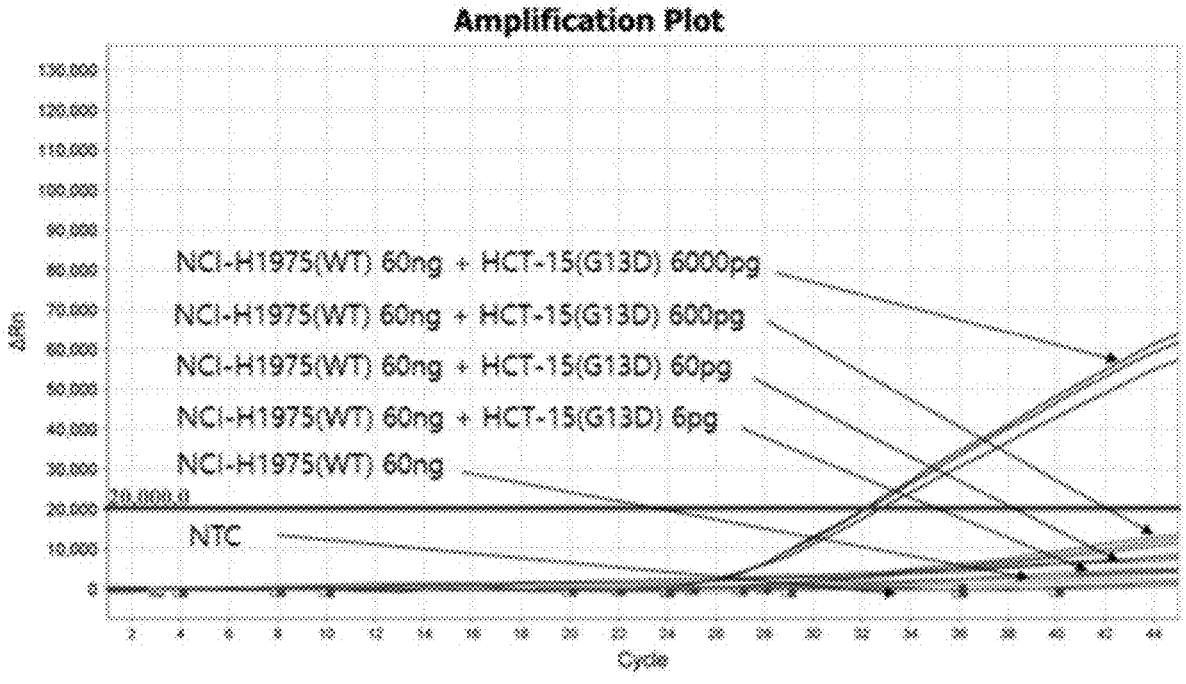

FIG. 5 is a presentation of PCR results measuring the genetic expression of KRAS G13D mutant mixed the wild-type KRAS gene using a KRAS wild-type single-stranded nucleic acid type 1 according to another embodiment of the present invention. Genomic DNA (gDNA) from HCT-15 cell-line was diluted to 10 to 0.01% with respect to the concentration of the genomic DNA (gDNA) from NCI-H1975. With the two genomic DNAs (gDNAs) mixed together and analyzed using the G13D single-stranded nucleic acid type 1 (SEQ ID NO: 7).

Figure 6:
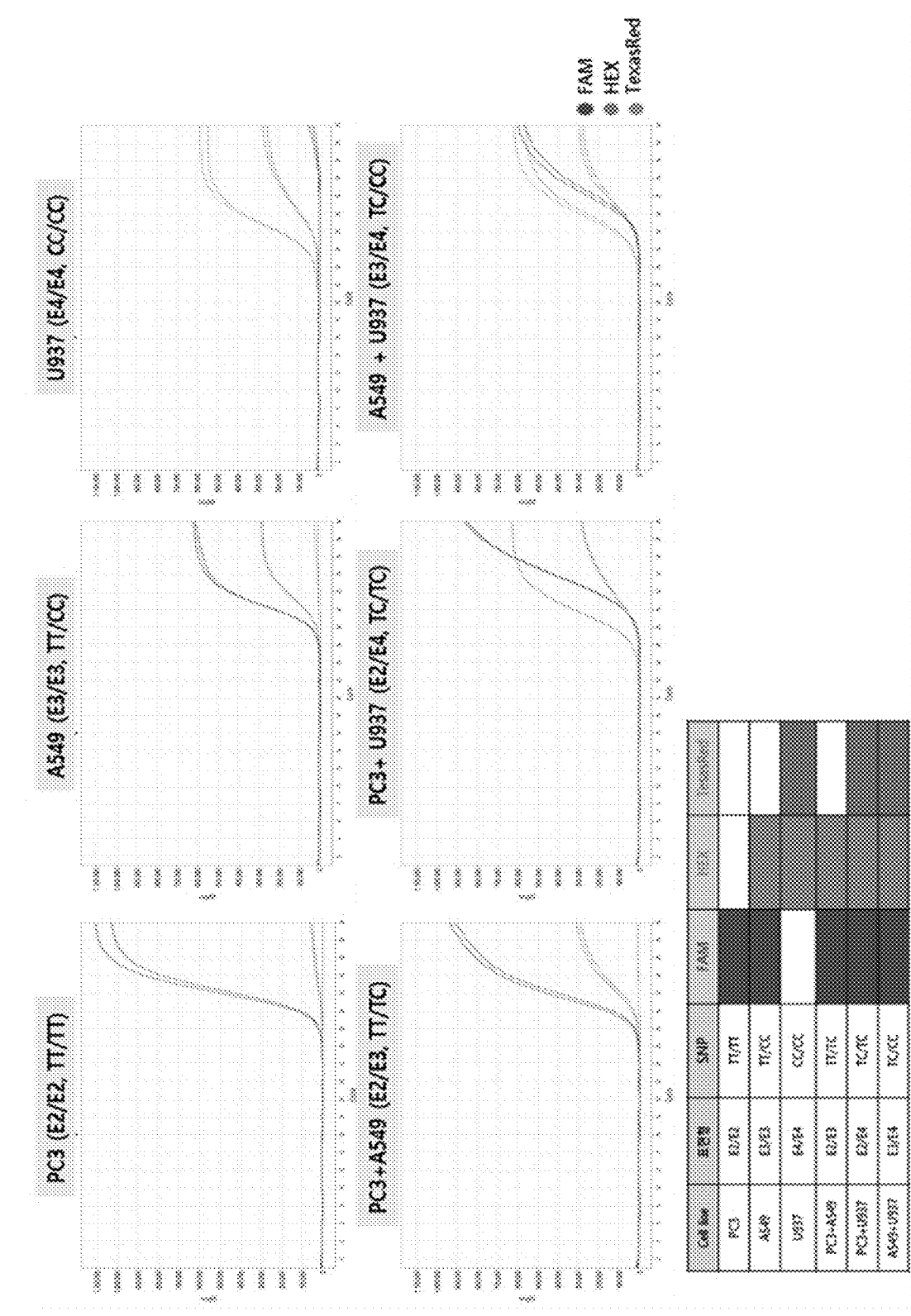

FIG. 6 is a presentation of PCR results measuring the genetic expression of ApoE gene using a single-stranded nucleic acid type 2 according to another embodiment of the present invention. According to the PCR results, the six ApoE genotypes (E2/E2, E3/E3, E4/E4, E2/E3, E2/E4, E3/E4) were discriminable by the use of the single-stranded nucleic acid type 2 (SEQ ID NO: 11, 12, 13, 14).

FIG. 7 is a presentation of PCR results measuring the genetic expression of KRAS G12V mutant using a single-stranded nucleic acid type 2 according to another embodiment of the present invention. Genomic DNA (gDNA) from SW620 cell-line harboring KRAS G12V mutant was diluted by concentrations, and PCR was carried out using a G12V single-stranded nucleic acid type 2 (SEQ ID NO: 15) to measure the genetic expression of G12V mutant on the function of the gDNA concentration.

FIG. 8 is a presentation of PCR results measuring the genetic expression of KRAS G12C mutant using a single-stranded nucleic acid type 2 according to another embodiment of the present invention. Genomic DNA (gDNA) from MIA-Paca2 cell-line harboring KRAS G12C mutant was diluted by concentrations, and PCR was carried out using a G12C single-stranded nucleic acid type 2 (SEQ ID NO: 16) to measure the genetic expression of G12C mutant on the function of the gDNA concentration.

Figure 9:
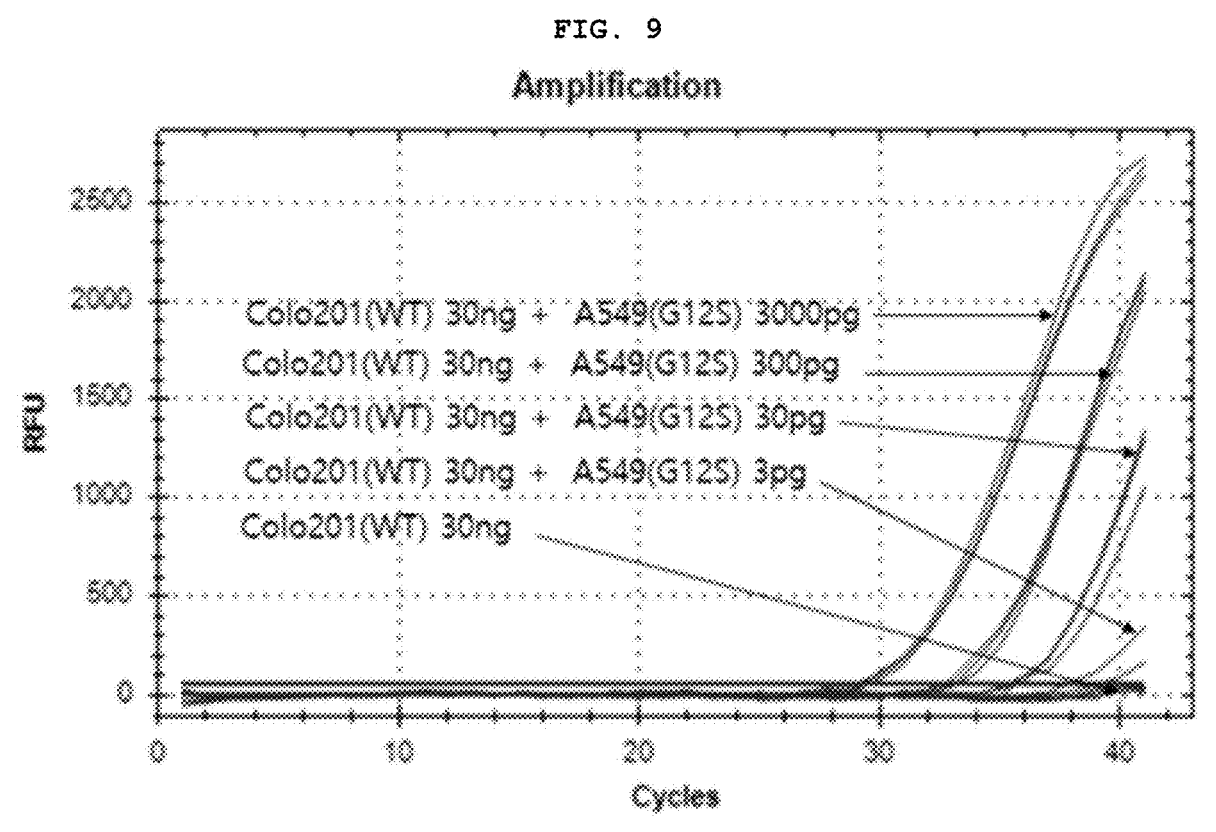

FIG. 9 is a presentation of PCR results measuring the genetic expression of KRAS G12S mutant using a single-stranded nucleic acid type 2 according to another embodiment of the present invention. Genomic DNA (gDNA) from A549 cell-line harboring KRAS G12S mutant was diluted by concentrations, and PCR was carried out using a G12S single-stranded nucleic acid type 2 (SEQ ID NO: 17) to measure the genetic expression of G12S mutant on the function of the gDNA concentration.

Figure 10:
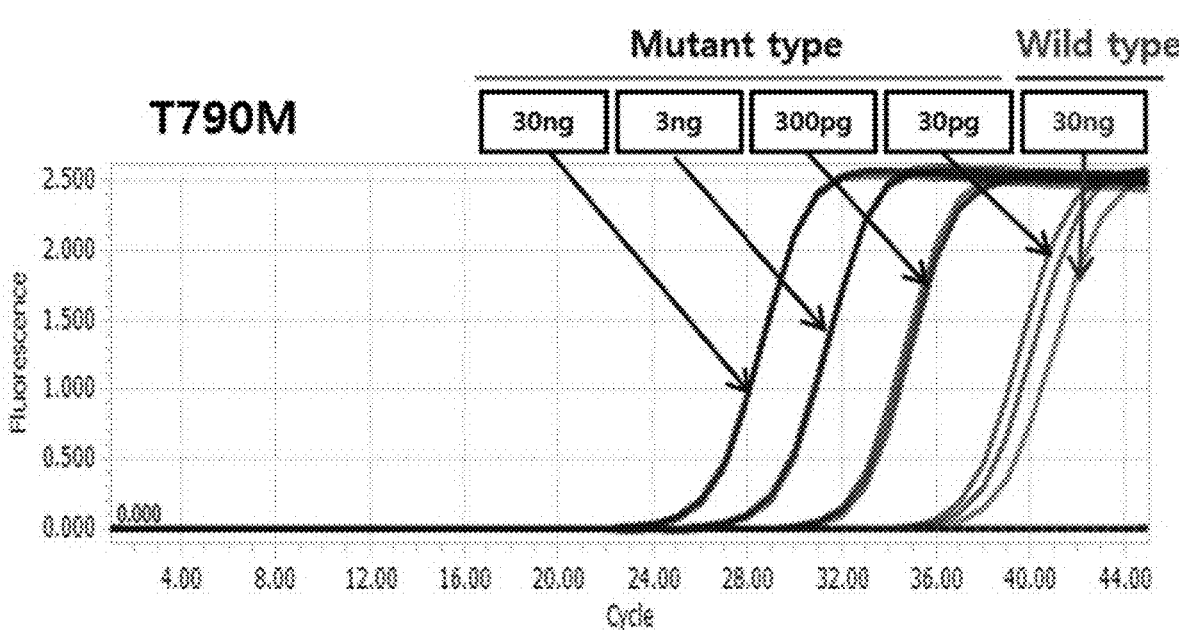

FIG. 10 is a presentation of PCR results measuring the genetic expression of EGFR T790M (in Exon 20) mutant using a single-stranded nucleic acid type 2 according to another embodiment of the present invention. Genomic DNAs (gDNAs) each from H1975 cell-line harboring EGFR T790M (in Exon 20) mutant or A549 wild-type cell-line were diluted by concentrations, and PCR was carried out using a T790M single-stranded nucleic acid (SEQ ID NO: 19) to measure the genetic expression of T790M mutant on the function of the gDNA concentration.

Figure 11:
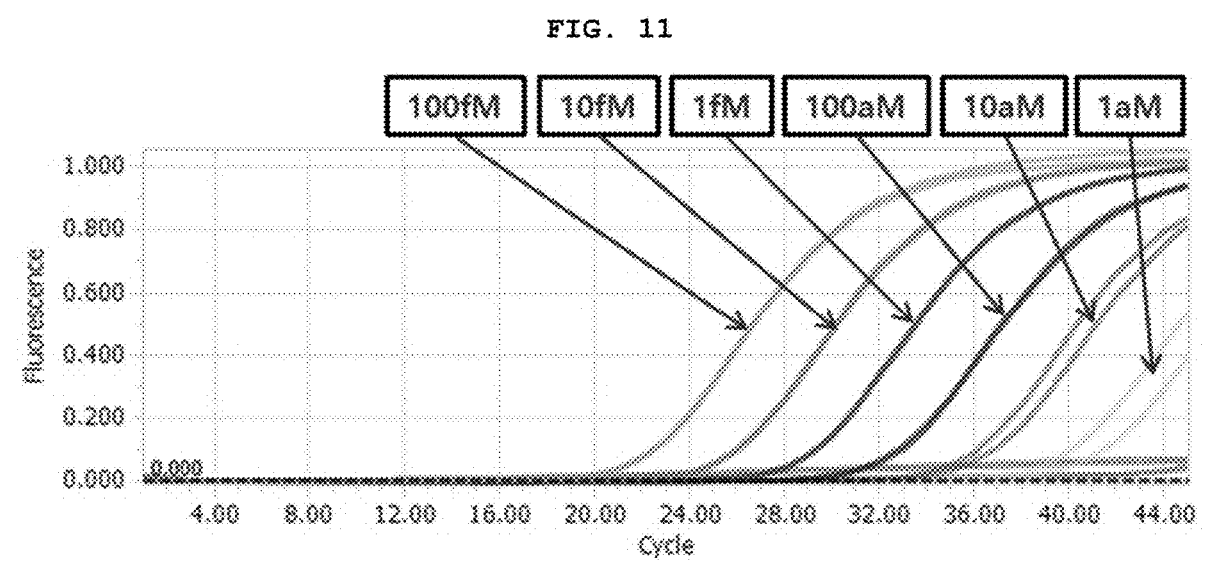

FIG. 11 is a presentation of PCR results measuring the genetic expression of let-7a miRNA using a single-stranded nucleic acid type 2 according to another embodiment of the present invention. let-7a cDNA synthesized from let-7a miRNA through RT-PCR was diluted by concentrations, and PCR was carried out using a let-7a single-stranded nucleic acid type 2 (SEQ ID NO: 21) to measure the genetic expression of let-7a miRNA on the function of the cDNA concentrations.

Figure 12:
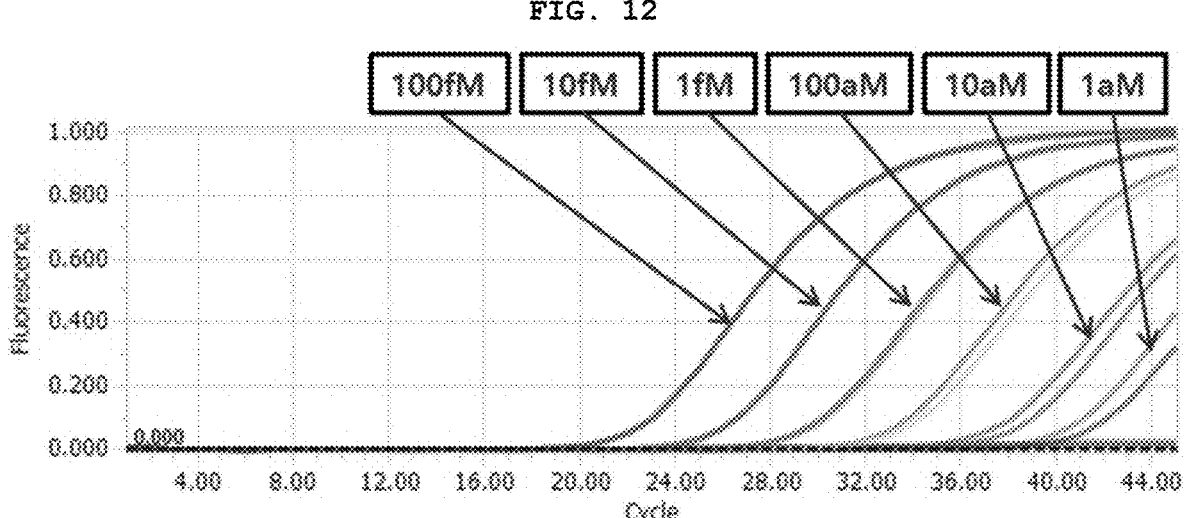

FIG. 12 is a presentation of PCR results measuring the genetic expression of let-7d miRNA using a single-stranded nucleic acid type 2 according to another embodiment of the present invention. let-7d cDNA synthesized from let-7d miRNA through RT-PCR was diluted by concentrations, and PCR was carried out using a let-7d single-stranded nucleic acid type 2 (SEQ ID NO: 24) to measure the genetic expression of let-7d miRNA on the function of the cDNA concentrations.

Figure 13:
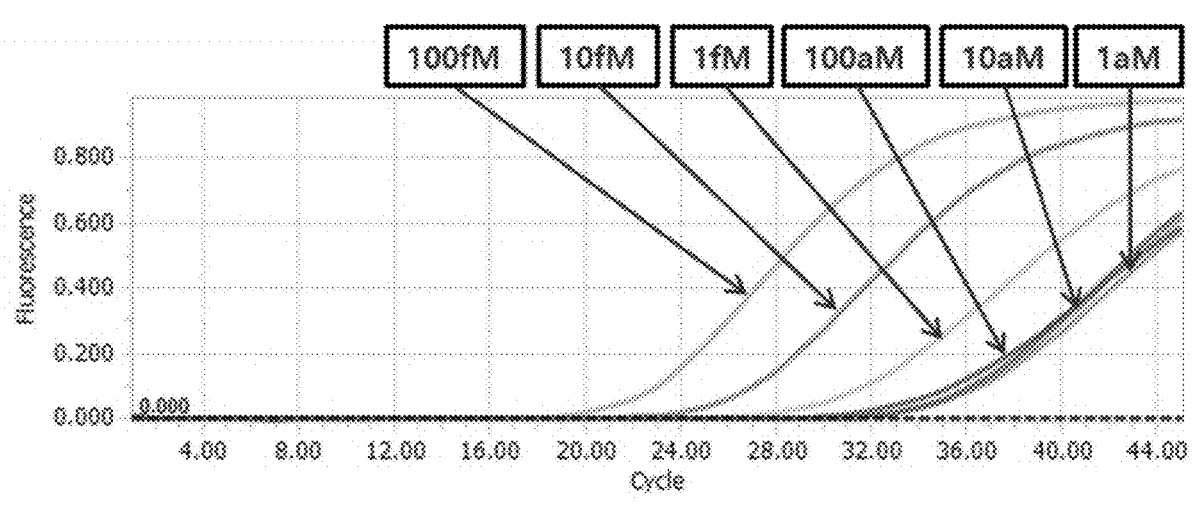

FIG. 13 is a presentation of PCR results measuring the performance of detection specific to let-7 miRNA using a single-stranded nucleic acid type 2 according to another embodiment of the present invention. let-7a cDNA was diluted by concentrations in the presence of let-7d cDNA (1 pM), and PCR was carried out using a let-7a single-stranded nucleic acid (SEQ ID NO: 21) to measure the genetic expression of let-7a miRNA as the function of the cDNA concentration, that is, the detection specific to let-7a miRNA in the presence of let-7d cDNA.

Figure 14:
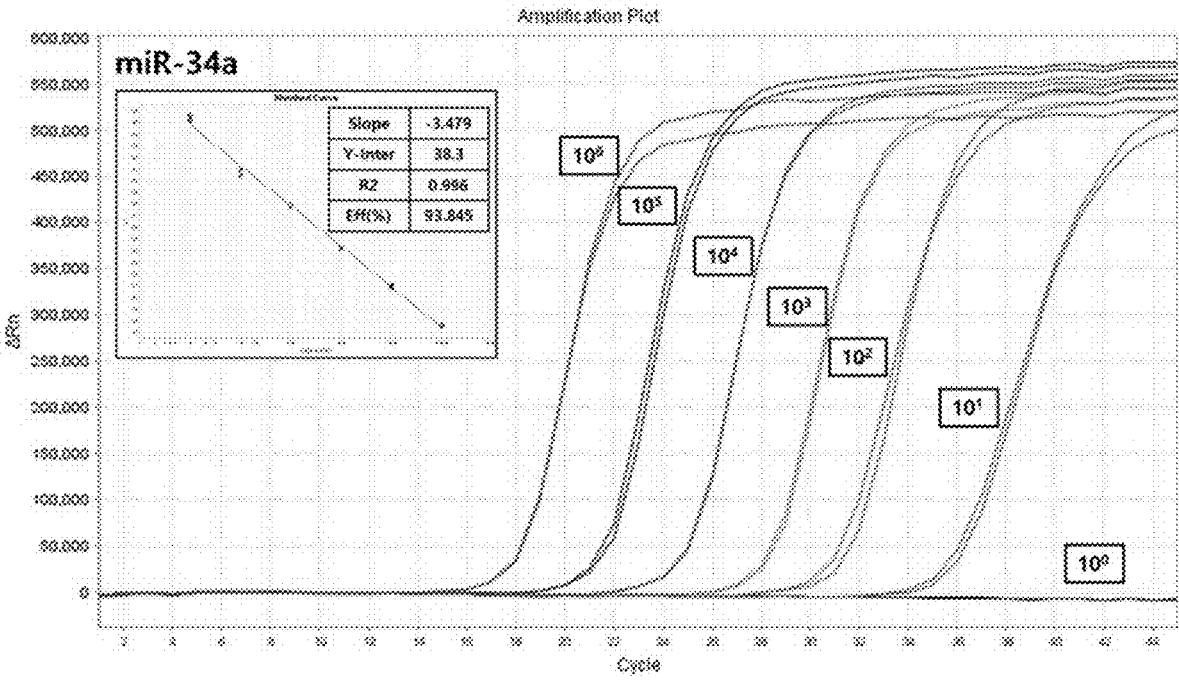

FIG. 14 is a presentation of PCR results measuring the genetic expression of miRNA 34a using a single-stranded nucleic acid type 2 according to another embodiment of the present invention. miRNA 34a cDNA synthesized from miRNA 34a through RT-PCR was diluted by concentrations, and PCR was carried out using a miRNA 34a single-stranded nucleic acid type 2 (SEQ ID NO: 27) to measure the genetic expression of miRNA 34a as a function of the cDNA concentration.

Figure 15:
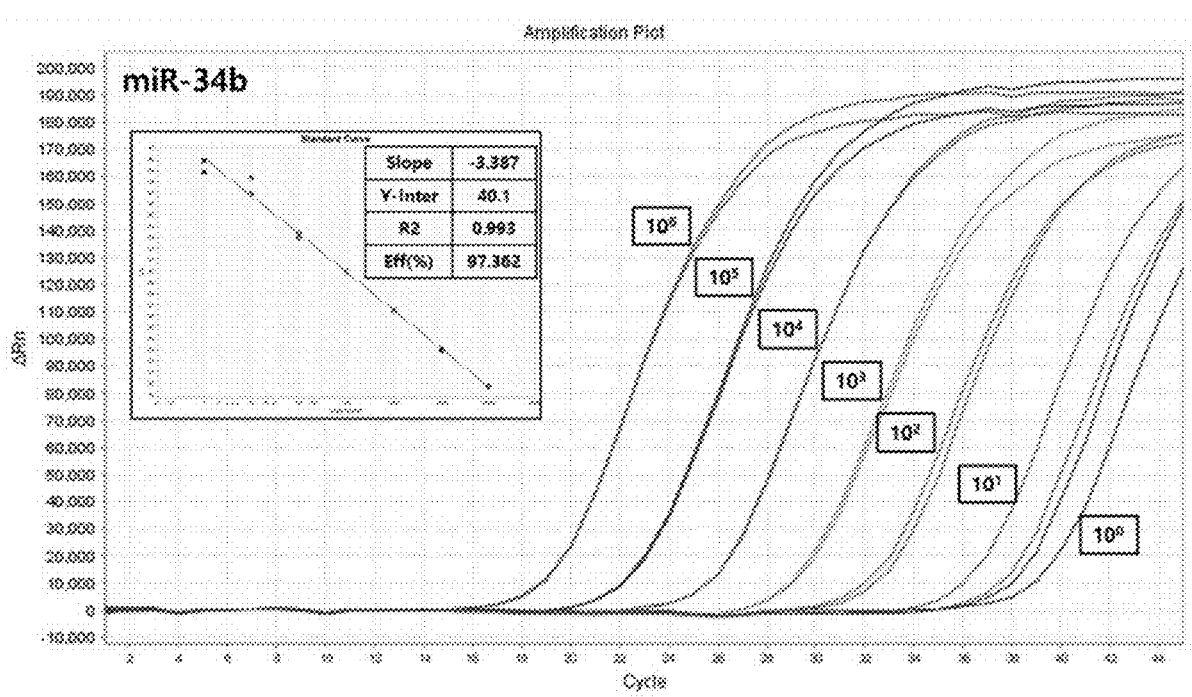

FIG. 15 is a presentation of PCR results measuring the genetic expression of miRNA 34b using a single-stranded nucleic acid type 2 according to another embodiment of the present invention. miRNA 34b cDNA synthesized from miRNA 34b through RT-PCR was diluted by concentrations, and PCR was carried out using a miRNA 34b single-stranded nucleic acid type 2 (SEQ ID NO: 30) to measure the genetic expression of miRNA 34b as a function of the cDNA concentration.

Figure 16:
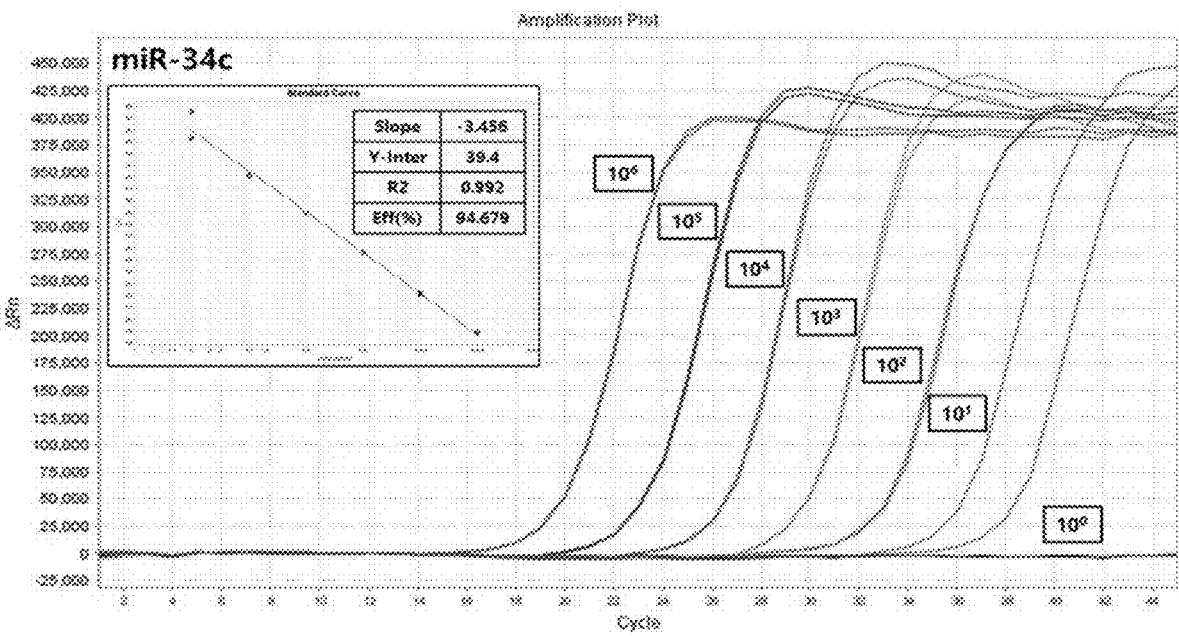

FIG. 16 is a presentation of PCR results measuring the genetic expression of miRNA 34c using a single-stranded nucleic acid type 2 according to another embodiment of the present invention. miRNA 34c cDNA synthesized from miRNA 34c through RT-PCR was diluted by concentrations, and PCR was carried out using a miRNA 34c single-stranded nucleic acid type 2 (SEQ ID NO: 33) to measure the genetic expression of miRNA 34c as a function of the cDNA concentration.

Figure 17:
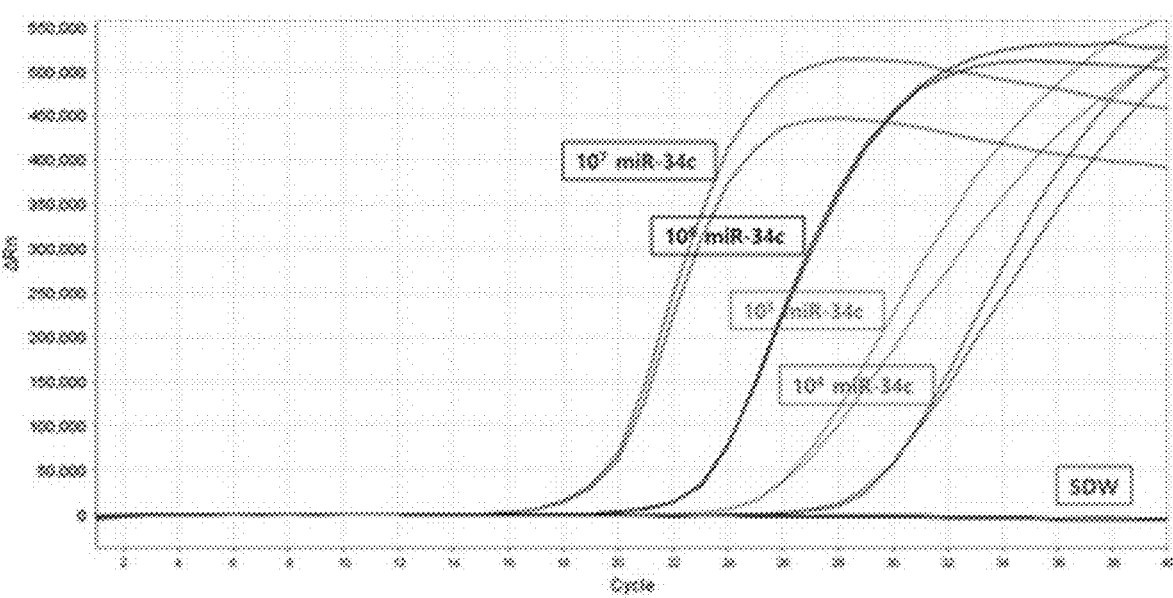

FIG. 17 is a presentation of PCR results measuring the performance of detection specific to miRNA 34 using a single-stranded nucleic acid type 2 according to another embodiment of the present invention. miRNA 34c cDNA was diluted by concentrations in the presence of miRNA 34a cDNA (100 pM), and PCR was carried out using a miRNA 34c single-stranded nucleic acid type 2 (SEQ ID NO: 33) to measure the genetic expression of miRNA 34c as the function of the cDNA concentration, that is, the detection specific to miRNA 34c in the presence of miRNA 34a cDNA.

Figure 18:
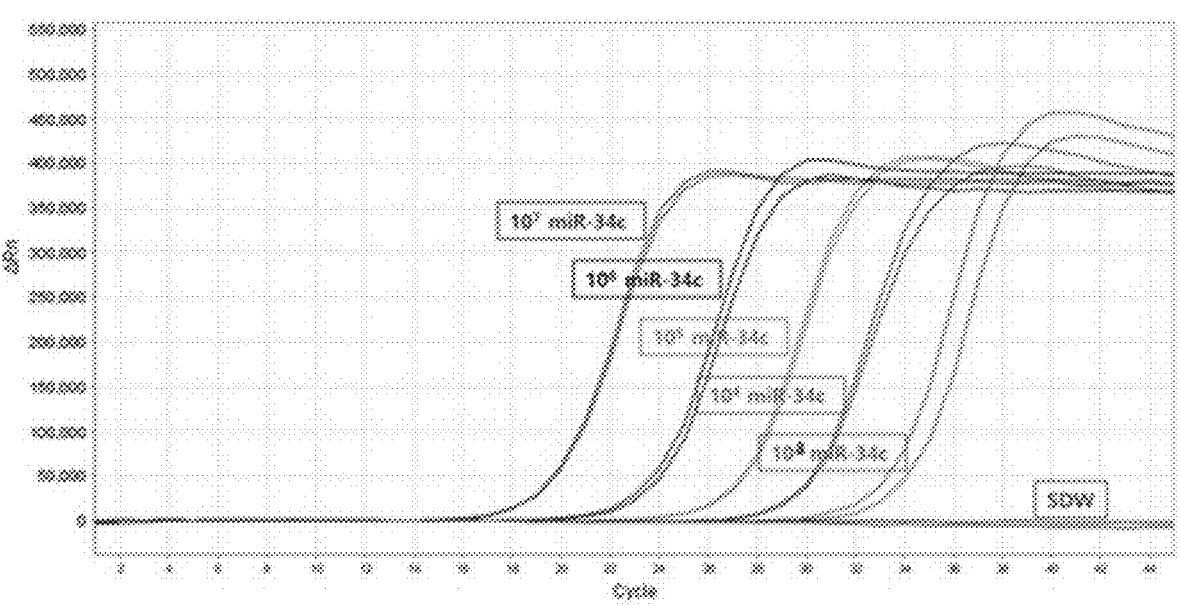

FIG. 18 is a presentation of PCR results measuring the performance of detection specific to miRNA 34 using a single-stranded nucleic acid type 2 according to another embodiment of the present invention. miRNA 34c cDNA was diluted by concentrations in the presence of miRNA 34b cDNA (100 pM), and PCR was carried out using a miRNA 34c single-stranded nucleic acid type 2 (SEQ ID NO: 33) to measure the genetic expression of miRNA 34c as the function of the cDNA concentration, that is, the detection specific to miRNA 34c in the presence of miRNA 34b cDNA.

Figure 19:
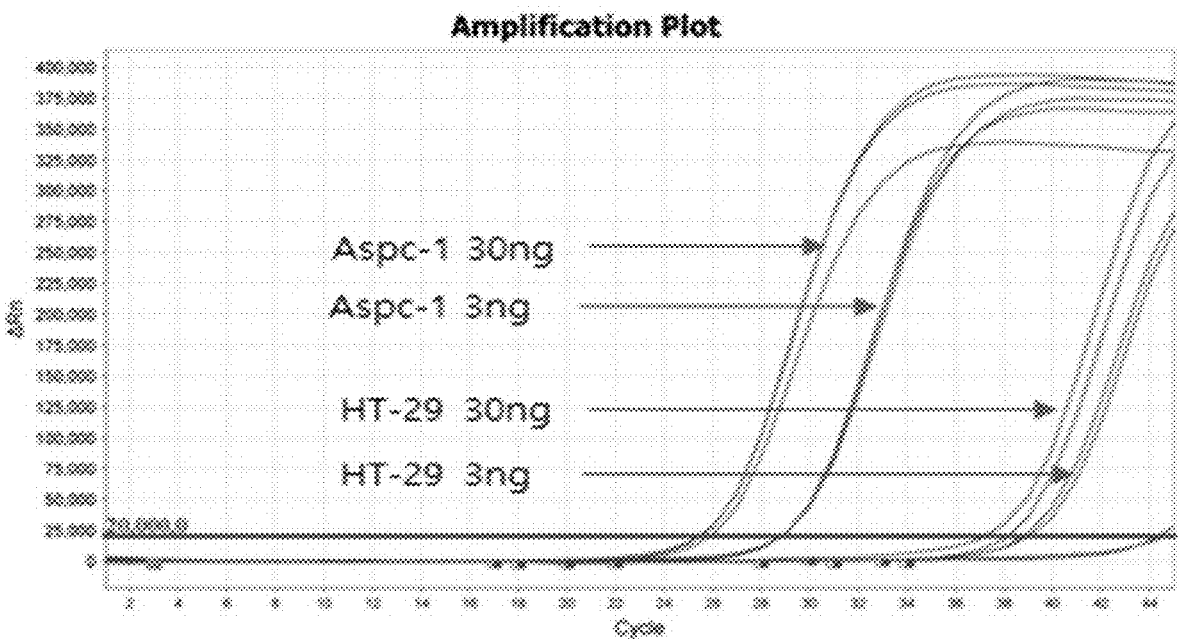

FIG. 19 is a presentation of PCR results measuring the genetic expression of KRAS G12D mutant using a DNAoligo-DNA-RNA-mutant-DNAoligo type KRAS G12D single-stranded nucleic acid type 2 (G12D-R1DrMR2) according to another embodiment of the present invention. Genomic DNAs (gDNAs) each from G12D-mutant Aspc-1 cell-line or KRAS wild-type HT-29 cell-line were diluted by concentrations, and PCR was carried out using a G12D single-stranded nucleic acid (SEQ ID NO: 36) to measure the genetic expression of G12D mutant on the function of the gDNA concentration.

Figure 20:
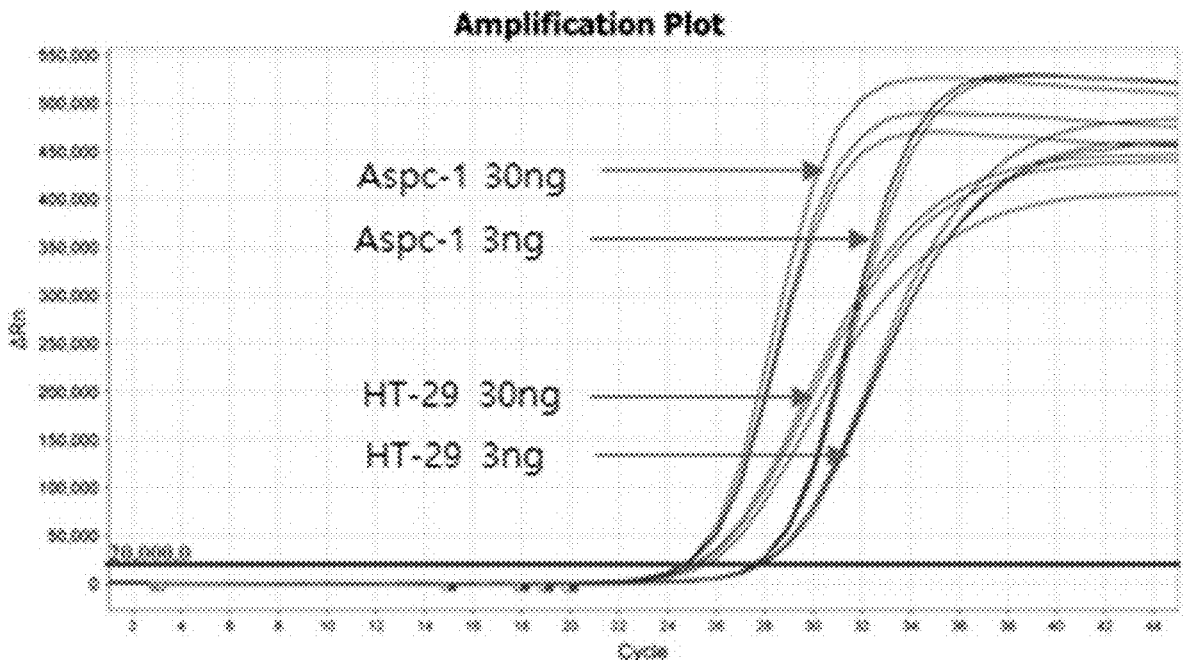

FIG. 20 is a presentation of PCR results measuring the genetic expression of KRAS G12D mutant using a DNAoligo-RNA-DNA-mutant-DNAoligo type KRAS G12D single-stranded nucleic acid type (G12D-R1rDMR2) according to another embodiment of the present invention. Genomic DNAs (gDNAs) each from G12D-mutant Aspc-1 cell-line or KRAS wild-type HT-29 cell-line were diluted by concentrations, and PCR was carried out using a G12D single-stranded nucleic acid (SEQ ID NO: 37) to measure the genetic expression of G12D mutant on the function of the gDNA concentration.

Figure 21:
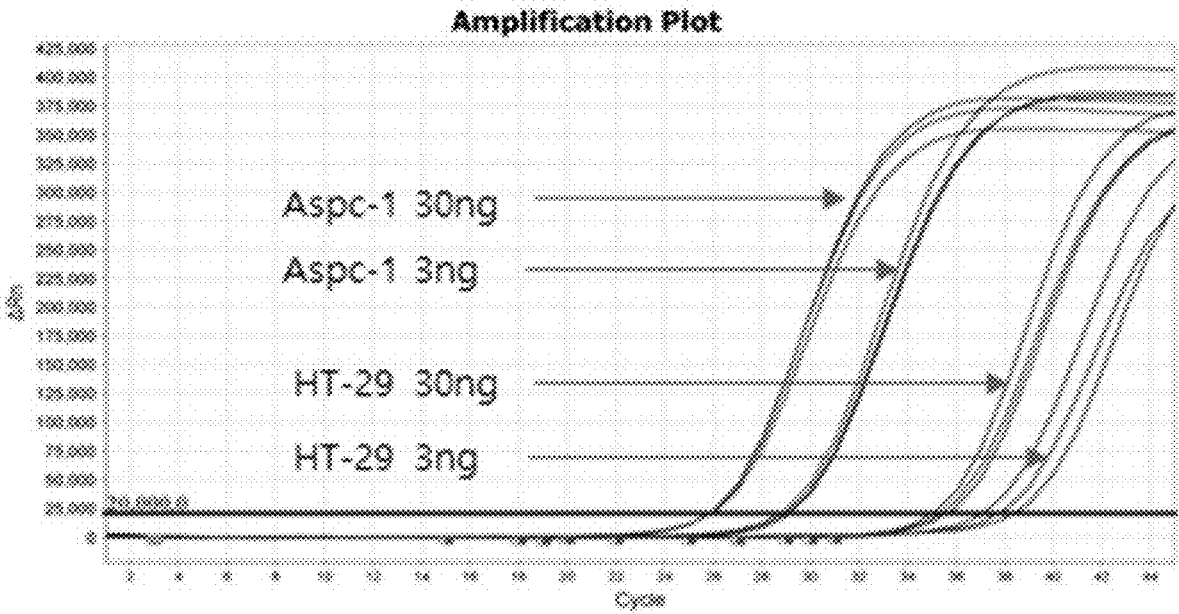

FIG. 21 is a presentation of PCR results measuring the genetic expression of KRAS G12D mutant using a DNAoligo-DNA-mutant-RNA-DNA-DNAoligo type KRAS G12D single-stranded nucleic acid type 2 (G12D-R1DMrDR2) according to another embodiment of the present invention. Genomic DNAs (gDNAs) each from G12D-mutant Aspc-1 cell-line or KRAS wild-type HT-29 cell-line were diluted by concentrations, and PCR was carried out using a G12D single-stranded nucleic acid (SEQ ID NO: 38) to measure the genetic expression of G12D mutant on the function of the gDNA concentration.

BEST MODES FOR CARRYING OUT THE INVENTION

The present invention is directed to a single-stranded nucleic acid for real-time detection of a genetic variation of a single target gene and a detection method using the same, and more particularly to a method for real-time detection of a genetic variation of a single target gene using a single-stranded nucleic acid and a kit for the same, where the method uses a single-stranded nucleic acid having a structure of X-Y-Z and a nucleotide sequence that can form a complementary bond to all or part of the nucleotide sequence of the single target gene containing a genetic variation such as single nucleotide polymorphism (SNP), point mutation, or miRNA isoform.

In one aspect, the present invention provides a single-stranded nucleic acid for detection of a genetic variation of a single target gene.

In the present invention, the single-stranded nucleic acid may have: (i) a structure of X-Y-Z; (ii) a complementary bonding to all or part of the nucleotide sequence of a single target gene containing a genetic variation; and (iii) at least two identical or different detectable markers attached to both ends or the inside thereof.

The positions of the attached detectable markers are not limited to particular positions and may be any positions at which the detectable markers can be separated when the Y region is cut out by a cleavage reagent.

The single-stranded nucleic acid forms a complementary bonding to all or part of the nucleotide sequence of the single target gene containing a genetic variation to be detected in real time, creating a complex with the single target gene and allowing for amplification.

In the present invention, the single-stranded nucleic acid refers to a nucleic acid designed to detect the presence of single nucleotide polymorphism (SNP), point mutation, or miRNA isoform in the detection of a genetic variation. In this regard, the single-stranded nucleic acid for detecting the presence of SNP is referred to as "type 1 single-stranded nucleic acid" or "single nucleic acid type 1"; and the single-stranded nucleic acid for detecting the presence of SNP or point mutation or miRNA isoform is referred to as "type 2 single-stranded nucleic acid" or "single-stranded nucleic acid type 2". Unlike the type 2 single-stranded nucleic acid, the type 1 single-stranded nucleic acid can act as a probe; and unlike the type 1 single-stranded nucleic acid, the type 2 single-stranded nucleic acid can function as a primer and a probe at once.

Specifically, when the Y region is cut out by a cleavage reagent, following the hybridization of the type 1 single-stranded nucleic acid with the single target gene, then both the X region and the Z region are separated from the single target gene so that the type 1 single-stranded nucleic acid can act as a probe. When the Y region is cut out by a cleavage reagent, following the hybridization of the type 2 single-stranded nucleic acid with the single target gene, then the Z region other than the X region is separated from the single target gene so that the type 2 single-stranded nucleic acid can act as a primer and a probe at the same time.

The single-stranded nucleic acid of the present invention has a structure of X-Y-Z, where each of X, Y and Z may have a different number of nucleotides.

The Y region is an RNA having a genetic sequence of one or two nucleotides at a locus of the single target gene. The Y region can be cut out by a cleavage reagent.

The cleavage reagent as used herein is preferably an agent for cleavage mediated by an enzyme, such as DNase, RNase, helicase, exonuclease, or endonuclease, and may include any known cleavage reagent.

The X region is a DNA having a genetic sequence of nucleotides. When the presence of single nucleotide polymorphism (SNP) is detected, the X may be a DNA having a genetic sequence of 4 to 20 nucleotides, preferably 4 to 19 nucleotides, more preferably 4 to 18 nucleotides, 5 to 18 nucleotides, 6 to 18 nucleotides, 6 to 17 nucleotides, or 6 to 16 nucleotides, and most preferably 6 to 15 nucleotides. The In this case, the X belongs to the type 1 single-stranded nucleic acid.

When the presence of single nucleotide polymorphism (SNP) or point mutation or miRNA isoform is detected, the X may be a DNA having a genetic sequence of 10 to 30 nucleotides, preferably 11 to 30 nucleotides, more preferably 12 to 30 nucleotides, 13 to 30 nucleotides, 14 to 30 nucleotides, 15 to 30 nucleotides, 15 to 29 nucleotides, 15 to 28 nucleotides, 15 to 27 nucleotides, 15 to 26 nucleotides, 15 to 25 nucleotides, 15 to 24 nucleotides, 15 to 23 nucleotides, 15 to 22 nucleotides, or 15 to 21 nucleotides, and most preferably 15 to 20 nucleotides. In this case, the X belongs to the type 2 single-stranded nucleic acid.

When the presence of single nucleotide polymorphism (SNP) is detected, the Z may be a DNA having a genetic sequence of 4 to 20 nucleotides, preferably 4 to 19 nucleotides, more preferably 4 to 18 nucleotides, 5 to 18 nucleotides, 6 to 18 nucleotides, 6 to 17 nucleotides, or 6 to 16 nucleotides, and most preferably 6 to 15 nucleotides. In this case, the Z belongs to the type 1 single-stranded nucleic acid.

When the presence of single point mutation or miRNA isoform is detected, the Z may be a DNA having a genetic sequence of 1 to 5 nucleotides, preferably 2 to 5 nucleotides, more preferably 2 to 4 nucleotides, and most preferably 2 to 3 nucleotides. In this case, the Z belongs to the type 2 single-stranded nucleic acid.

In the present invention, the detection of a genetic variation is to detect the presence of single nucleotide polymorphism (SNP), point mutation, or miRNA isoform. The genetic variation can be detected with specificity and sensitivity depending on the number of nucleotides constituting the X region and the Z region in the single-stranded nucleic acid.

Figure 1:
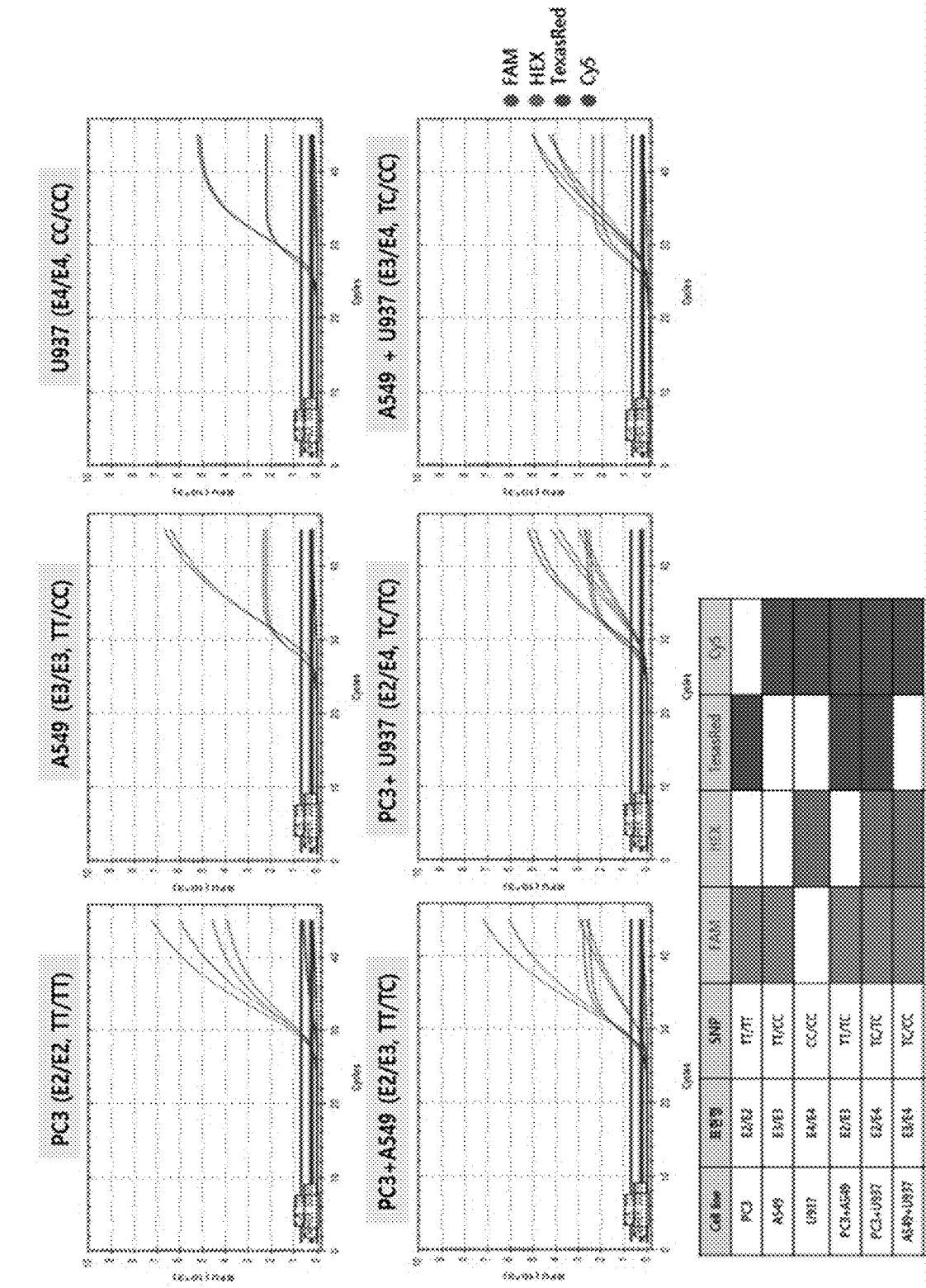
FIG. 1 is a presentation of PCR results for measuring the genetic expression of ApoE gene using a single-stranded nucleic acid according to one embodiment of the present invention. According to the PCR results, the six ApoE genotypes (E2/E2, E3/E3, E4/E4, E2/E3, E2/E4, E3/E4) were discriminable by the use of the ApoE single-stranded nucleic acid type 1 (SEQ ID NO: 3, 4, 5, 6).

In one embodiment of the present invention, according to the real-time PCR, the six ApoE genotypes (E2/E2, E3/E3, E4/E4, E2/E3, E2/E4, E3/E4) were precisely discriminable due to the use of the ApoE single-stranded nucleic acids (SEQ ID NO: 3, 4, 5, 6) (FIG. 1).

In another embodiment of the present invention, genomic DNA (gDNA) from SW620 cell-line harboring KRAS G12V mutant was diluted by concentrations, and a real-time PCR was carried out using a G12V single-stranded nucleic acid type 2 (SEQ ID NO: 15) to measure the genetic expression of G12V mutant on the function of the gDNA concentration (FIG. 7).

In another embodiment of the present invention, genomic DNA (gDNA) from MIA-Paca2 cell-line harboring KRAS G12C mutant was diluted by concentrations, and a real-time PCR was carried out using a G12C single-stranded nucleic acid (SEQ ID NO: 16) to measure the genetic expression of G12C mutant on the function of the gDNA concentration (FIG. 8).

In another embodiment of the present invention, genomic DNA (gDNA) from A549 cell-line harboring KRAS G12S mutant was diluted by concentrations, and a real-time PCR was carried out using a G12S single-stranded nucleic acid (SEQ ID NO: 17) to measure the genetic expression of G12S mutant on the function of the gDNA concentration (FIG. 9).

In another embodiment of the present invention, genomic DNAs (gDNAs) each from H1975 cell-line harboring EGFR T790M (in Exon 20) mutant or A549 wild-type cell-line were diluted by concentrations, and a real-time PCR was carried out using a T790M single-stranded nucleic acid (SEQ ID NO: 19) to measure the genetic expression of T790M mutant on the function of the gDNA concentration (FIG. 10).

In another embodiment of the present invention, let-7a cDNA was diluted by concentrations, and a real-time PCR was carried out using a let-7a single-stranded nucleic acid (SEQ ID NO: 21) to measure the genetic expression of let-7a miRNA on the function of the cDNA concentration (FIG. 11).

In another embodiment of the present invention, let-7d cDNA was diluted by concentrations, and a real-time PCR was carried out using a let-7d single-stranded nucleic acid type 2 (SEQ ID NO: 24) to measure the genetic expression of let-7d miRNA on the function of the cDNA concentrations (FIG. 12).

In another embodiment of the present invention, 2 μl of diluted let-7a cDNA (100 fM to 1 aM) was added to 2 μl of let-7d cDNA (1 pM) in the test group, and let-7a cDNA was detected at concentrations of 100 fM to 1 fM (FIG. 13).

In another embodiment of the present invention, miRNA 34a cDNA was diluted by concentrations, and a real-time PCR was carried out using a miRNA 34a single-stranded nucleic acid (SEQ ID NO: 27) to measure the genetic expression of miRNA 34a as a function of the cDNA concentration (FIG. 14).

In another embodiment of the present invention, miRNA 34b cDNA was diluted by concentrations, and a real-time PCR was carried out using a miRNA 34b single-stranded nucleic acid (SEQ ID NO: 30) to measure the genetic expression of miRNA 34b as a function of the cDNA concentration (FIG. 15).

In another embodiment of the present invention, miRNA 34c cDNA was diluted by concentrations, and a real-time PCR was carried out using a miRNA 34c single-stranded nucleic acid (SEQ ID NO: 33) to measure the genetic expression of miRNA 34c as a function of the cDNA concentration (FIG. 16).

In another embodiment of the present invention, miRNA 34c cDNA was diluted by concentrations in the presence of miRNA 34a cDNA or miRNA 34b cDNA, and a real-time PCR was carried out using a miRNA 34c single-stranded nucleic acid (SEQ ID NO: 33), showing that the genetic expression of miRNA 34c was detectable at extremely low concentrations (FIGS. 17 and 18).

In the present invention, the detectable markers may be either a fluorescent substance or a fluorescent pair of the fluorescent substance and a quencher, the fluorescent substance forming a covalent or non-covalent bond to the single-stranded nucleic acid.

The fluorescent substance may be, for example, any one selected from the group consisting of Cy®3 (sulfoindocarbocyanine dye), Cy®5 (sulfoindodicarbocyanine dye), Cy® 5.5 (sulfoindotricarbocyanine dye), Bodipy® (boron dipyrromethene), Alexa™ 488 (fluorescein derivative), Alexa™ 532 (rhodamine derivative), Alexa™ 546 (rhodamine derivative), Alexa™ 568 (rhodamine derivative), Alexa™ 594 (sulforhodamine derivative), Alexa™ 660 (cyanine dye derivative), RHODAMINE™ (Xanthene dye), TAMRA™ (5 (6)-Carboxytetramethylrhodamine). FAM™ (6-Carboxyfluorescein), FITC (fluorescein isothiocyanate), Fluor™ X (fluorescein derivative), ROX™ (6-carboxy-X-rhodamine), Texas Red™ (a mixture of isomeric sulfonyl chlorides and sulforhodamine; Invitrogen™), ORANGE GREEN 488X (fluorescein derivative), ORANGE GREEN 514X (fluorescein derivative), HEX™ (hexachloro-6-carboxyfluorescein), TET™ (tetrachloro-6-carboxyfluorescein), JOE™ (6-Carboxy-4', 5'-dichloro-2', 7'-dimethoxyfluorescein). Oyster® 556, Oyster® 645, Bodipy™ (boron dipyrromethene) 630/650, Bodipy™ (boron dipyrromethene). 650/665, Calfluor™ Orange 546 (proprietary fluorophores available from Biosearch Technologies, Inc.), Calfluor™ red 610 (proprietary fluorophores available from Biosearch Technologies, Inc.), Quasar® 670 (indocarbocyanine), and biotin, but is not necessarily limited thereto.

The quencher may be, for example, any one selected from the group consisting of DARK QUENCHER-1 (dimethylquench dye 1), Dabcyl (4-((4-of DEEP (Dimethylamino) phenyl)azo)benzoic acid). Eclipse™, 6-TAMRA™ (6-Carboxytetramethylrhodamine), BLACK HOLE QUENCHER®-1 (4-(4-dimethylaminophenylazo)benzoic acid), BLACK HOLE QUENCHER®-2 (3-[(4-dimethylaminophenyl)azo]-4-hydroxynaphthoic acid), BLACK HOLE QUENCHER®-3 (an extended azo-naphthol or anthraquinone derivative), IOWA BLACK® RQ-Sp (non-fluorescent arylazo dyes), QSY™-7 (N,N'-dimethyl-N, N'-diphenyl-4-((5-t-butoxycarbonylaminopentyl)aminocarbonyl) piperidinylsulfonerhodamine), QSY™-2 (N,N'-dimethyl-N,N'-diphenyl-(rhodamine core) derivative), and MGBNFQ (Minor Groove Binder Non-Fluorescent Quencher), but is not necessarily limited thereto.

When a fluorescent pair is used as the detectable marker in the present invention, the fluorescent substance and the quencher may be positioned in the X or Z region, and the positions thereof are not specifically limited. For example, the fluorescent substance may be positioned at the locus of the X region, and the quencher may be at the locus of the Y or Z region.

In detecting the presence of point mutation or miRNA isoform as a genetic variation of the single target gene, the single-stranded nucleic acid of the present invention may be used as: (i) an RT primer for synthesizing a cDNA from the RNA of the nucleic acid; (ii) a forward primer for amplifying the cDNA synthesized from the nucleic acid (DNA or RNA); (iii) a reverse primer for amplifying the cDNA synthesized from the nucleic acid (DNA or RNA); (iv) a forward primer and a reverse primer for amplifying the cDNA synthesized from the nucleic acid (DNA or RNA); or (v) a probe for real-time identification of the nucleic acid (DNA or RNA) to be detected.

In particular, when the single-stranded nucleic acid of the present invention is used as an RT primer; or a forward primer and a probe; or a reverse primer and a probe, for the purpose of synthesizing cDNA from RNA (including miRNA, etc.) and amplifying the synthesized cDNA, then there is no need for a process of fabricating the RT primer in the loop form or forming poly A in synthesis of cDNA; instead, the single-stranded nucleic acid is hybridized with the target RNA to be detected, only to ensure synthesis of cDNA and amplification and real-time detection of the RNA (including miRNA, etc.).

In another aspect, the present invention provides a real-time detection kit including the single-stranded nucleic acid for detecting the genetic variation of a single target gene.

When the single-stranded nucleic acid of the present invention is used as a kit for detecting the genetic variation of a single target gene, the kit may further include, in addition to the single-stranded nucleic acid of the present invention, an enzyme capable of cleaving the Y region of the single-stranded nucleic acid.

In the present invention, the enzyme capable of cleaving the Y region of the single-stranded nucleic acid may be any enzyme capable of specifically cleaving the Y region of the single-stranded nucleic acid. When the Y region is a DNA, for example, the enzyme capable of cleaving the Y region is preferably DNA nuclease (DNase), specifically DNase I, DNase II, S1 nuclease, nuclease P1, AP endonuclease, UvrABSC nuclease, etc. When the Y region is an RNA, the enzyme capable of cleaving the Y region is preferably ribonuclease (RNase), specifically RNase II, RNase III, RNase IV, RNase H, RNase T2, etc.

When the single-stranded nucleic acid is used as a kit for real-time detection of genetic variation of a single target gene according to the present invention, the kit may further include a reagent required for DNA amplification, in addition to the single-stranded nucleic acid of the present invention and the enzyme capable of cleaving the Y region of the single-stranded nucleic acid.

The reagent required for amplification includes, for example, suitable amounts of DNA polymerase (e.g., thermostable DNA polymerase derived from *Thermus aquaticus* (Taq), *Thermus thermophilus* (Tth), *Thermus filiformis, Thermis flavus, Thermococcus literalis*, or *Phyrococcus furiosis* (Pfu)), DNA polymerase cofactor (Mg$^{2+}$), buffer, dNTPs (dATP, dCTP, dGTP, and dTTP), and water (dH2O). In addition, the buffer includes, but is not limited to, suitable amounts of Triton X-100, dimethylsufoxide (DMSO), Tween 20, nonidet P40, PEG 6000, formamide, and bovine serum albumin (BSA).

In another aspect, the present invention provides a method for detecting a genetic variation of a single target gene that includes the steps of: (a) obtaining a target nucleic acid containing a genetic variation to be detected from a biological sample; (b) preparing the single-stranded nucleic acid; (c) mixing the target nucleic acid obtained in step (a) and the single-stranded nucleic acid prepared in step (b) with a primer set having a nucleotide sequence complementary to the target nucleic acid obtained in step (a) and a cleavage reagent, and then amplifying a complex of the target nucleic acid containing the genetic variation and the single-stranded nucleic acid by extension; and (d) determining the quantity of fragments of the single-stranded nucleic acid separated from the complex of the target nucleic acid containing the genetic variation and the single-stranded nucleic acid amplified in step (c).

Each step of the real-time detection method for genetic variation of a single target gene according to the present invention will now be described as follows.

The step (a) is obtaining, from a biological sample, a target nucleic acid containing a genetic variation to be detected.

In the present invention, the target nucleic acid containing the genetic variation may be an RNA or DNA to be detected from the sample, or a cDNA obtained by amplification of the RNA with a reverse transcription polymerase.

The sample may be either a biological sample, or RNA, DNA, or a fragment thereof, isolated from the biological sample. Specifically, the sample may be at least any one selected from the group consisting of blood, saliva, urine, feces, tissue, cell, and biopsy samples, or may also be RNA, DNA, or a fragment thereof, isolated from a stored biological sample, but is not necessarily limited thereto.

The stored biological sample may be one stored for at least one week, one year, for example, 1 to 10 years by any conventional method known in the art. Alternatively, the sample may be one derived from freeze-stored tissues or formalin-fixed tissues stored at room temperature.

In the present invention, the extraction of RNA or DNA from the sample may be performed using various methods known in the art.

The step (b) is preparing the single-stranded nucleic acid.

In the present invention, the single-stranded nucleic acid is as described above. Specifically, the single-stranded nucleic acid may have: (i) a structure of X-Y-Z; (ii) a complementary bonding to all or part of the nucleotide sequence of a single target gene containing a genetic variation; and (iii) at least two identical or different detectable markers attached to both ends or the inside thereof.

In the present invention, the detectable marker may be either a fluorescent substance or a fluorescent pair of the fluorescent substance and a quencher, the fluorescent substance forming a covalent or non-covalent bond to the single-stranded nucleic acid.

The fluorescent substance may be, for example, any one selected from the group consisting of Cy®3 (sulfoindocarbocyanine dye), Cy®5 (sulfoindodicarbocyanine dye), Cy® 5.5 (sulfoindotricarbocyanine dye), Bodipy® (boron dipyrromethene), Alexa™ 488 (fluorescein derivative), Alexa™ 532 (rhodamine derivative), Alexa™ 546 (rhodamine derivative), Alexa™ 568 (rhodamine derivative), Alexa™ 594 (sulforhodamine derivative), Alexa™ 660 (cyanine dye derivative), RHODAMINE™ (Xanthene dye), TAMRA™ (5(6)-Carboxytetramethylrhodamine), FAM™ (6-Carboxyfluorescein), FITC (fluorescein isothiocyanate), Fluor™ X (fluorescein derivative), ROX™ (6-carboxy-X-rhodamine), Texas Red™ (a mixture of isomeric sulfonyl chlorides and sulforhodamine; Invitrogen™), ORANGE GREEN 488X (fluorescein derivative), ORANGE GREEN 514X (fluorescein derivative), HEX™ (hexachloro-6-carboxyfluorescein), TET™ (tetrachloro-6-carboxyfluorescein), JOE™ (6-Carboxy-4',5'-dichloro-2',7'-dimethoxyfluorescein) Oyster® 556, Oyster® 645, Bodipy™ (boron dipyrromethene) 630/650, Bodipy™ (boron dipyrromethene) 650/665, Calfluor™ Orange 546(proprietary fluorophores available from Biosearch Technologies, Inc.), Calfluor™ red 610 (proprietary fluorophores available from Biosearch Technologies, Inc.), Quasar® 670 (indocarbocyanine), and biotin but is not necessarily limited thereto. The quencher as used herein may be, for example, any one selected from the group consisting of D DEEP DARK QUENCHER-1 (dimethylquench dye 1), Dabcyl (4-((4-(Dimethylamino)phenyl)azo)benzoic acid), Eclipse™ 6-TAMRA™ (6-Carboxytetramethylrhodamine), BLACK HOLE QUENCHER®-1 (4-(4-dimethylaminophenylazo) benzoic acid), BLACK HOLE QUENCHER®-2 (3-[(4-dimethylaminophenyl)azo]-4-hydroxynaphthoic acid), BLACK HOLE QUENCHER®-3 (an extended azo-naphthol or anthraquinone derivative), IOWA BLACK® RQ-Sp (non-fluorescent arylazo dyes), QSY™-7 (N,N'-dimethyl-N, N'-diphenyl-4-((5-t-butoxycarbonylaminopentyl)aminocarbonyl)piperidinylsulfonerhodamine), QSY™-2 N,N'-dimethyl-N, N'-diphenyl-(rhodamine core) derivative), and MGBNFQ (Minor Groove Binder Non-Fluorescent Quencher), but is not necessarily limited thereto.

The step (c) is amplifying the complex of the target nucleic acid containing a genetic variation and the single-stranded nucleic acid.

In the present invention, the amplification of the complex of the target nucleic acid containing a genetic variation and the single-stranded nucleic acid may be carried out by extension after mixing the extracted target nucleic acid and the synthesized single-stranded nucleic acid with a primer set having a nucleotide sequence complementary to the extracted target nucleic acid and a cleavage reagent.

In the present invention, the cleavage reagent is preferably a cleavage reagent performing a cleavage mediated by an enzyme, but any known cleavage reagents may also be used. In this regard, the cleaving of RNA or DNA catalyzed by the enzymes, such as DNase, RNase, helicase, exonuclease, and endonuclease, is referred to as "enzyme-mediated cleavage". In one preferred embodiment of the present invention, nicking and cleaving of the hybridized probe is more preferably catalyzed by endonuclease or exonuclease. The ribonuclease is more preferably a double-stranded ribonuclease that activates nicking and cleaving of ribonucleic acid from double-stranded DNA-RNA complex strands.

In the present invention, the cleavage reagent may be, if is not limited to, ribonuclease (RNase), such as RNaseH, RNase II, RNase III, RNase IV, or RNase T2.

The step (d) is determining the quantity of fragments of the single-stranded nucleic acid separated from the amplified complex of the target nucleic acid containing a genetic variation and the single-stranded nucleic acid.

In the present invention, the measurement of the amount of fragments of the single-stranded nucleic acid may be performed using various detection methods. Specifically, the quantity of fragments of the single-stranded nucleic acid cleaved according to the present invention is preferably measured in real time or after completion of the reaction, and may be determined by measuring a change in fluorescence intensity or measuring chemiluminescence.

The measurement of the change in fluorescence intensity or chemiluminescence may be performed using any measurement equipment capable of detecting a fluorescent marker, as known in the art. For example, the measurement may be performed using a TRIAD multimode detector, a Wallac/Victor fluorescence or Perkin-Elmer LB50B luminescence spectrometer, LightCycler 96, Applied Biosystems 7500, or Biorad CFX96 real-time PCR thermocycler, but is not limited thereto.

The measurement and detection method for the amount of fragments of the single-stranded nucleic acid cleaved according to the present invention may vary depending on the kind of the label or detectable marker introduced into the single-stranded nucleic acid or the reaction solution.

The amplification step following the cleavage of the Y region of the single-stranded nucleic acid of the present invention makes the genetic variation in the Y region more discriminable, so the mutation can be detected through the subsequent amplification of nucleic acids. That is, when hybridization is formed between the Y region of the single-stranded nucleic acid of the present invention and the genetic variation region of target nucleic acid, the Y region is cleaved only when exactly complementary to the genetic variation region of target nucleic acid, and then the amplification reaction is activated so that the presence of the genetic variation can be precisely determined. Specifically, even if the Y region of the single-stranded nucleic acid of the present invention and the genetic variation region of target nucleic acid are allowed to hybridize, the Y region is not cleaved and the amplification reaction does not occur in case that the Y region does not have a complementary binding. It means that there is no genetic variation to be detected in the target nucleic acid. In contrast, even if the Y region of the single-stranded nucleic acid of the present invention and the genetic variation region of target nucleic acid, which is not mutated, are allowed to hybridize, the Y region is not cleaved and the amplification reaction does not occur in case that the Y region does not have a complementary binding. It means that there is no genetic variation to be detected in the target nucleic acid.

In the present invention, the detection of the genetic variation is detecting the presence of single nucleotide polymorphism (SNPs), point mutations, or miRNA isoforms.

In one embodiment of the present invention, gDNAs each synthesized from G12D-mutant Aspc-1 cell-line or KRAS wild-type HT-29 cell-line were diluted by concentrations, and real-time PCR was carried out using a DNAoligo-DNA-RNA-mutant-DNAoligo type KRAS G12D single-stranded nucleic acid (G12D-R1DrMR2; sequence number 36) to measure the genetic expression of G12D mutant as a function of the gDNA concentration (FIG. 19).

In another embodiment of the present invention, gDNAs each synthesized from G12D-mutant Aspc-1 cell-line or KRAS wild-type HT-29 cell-line were diluted by concentrations, and real-time PCR was carried out using a DNAoligo-RNA-DNA-mutant-DNAoligo type KRAS G12D single-stranded nucleic acid (G12D-R1rDMR2; sequence number 37) to measure the genetic expression of G12D mutant as a function of the gDNA concentration (FIG. 20).

In another embodiment of the present invention, gDNAs each synthesized from G12D-mutant Aspc-1 cell-line or KRAS wild-type HT-29 cell-line were diluted by concentrations, and real-time PCR was carried out using a DNAoligo-DNA-mutant-RNA-DNA-DNAoligo type KRAS G12D single-stranded nucleic acid (G12D-R1DMrDR2; sequence number 38) to measure the genetic expression of G12D mutant as a function of the gDNA concentration (FIG. 21).

The extension reaction, namely, nucleic acid amplification as available in the present invention with ease is known to those skilled in the related art. That is, amplification of the target nucleic acid may be performed by one method selected from the group consisting of polymerase chain reaction (PCR), rolling circle amplification (RCA), strand displacement amplification (SDA), and nucleic acid sequence-based amplification (NASBA), but is not necessarily limited thereto. The product of the nucleic acid amplification is a DNA or RNA.

Generally, the reaction solution contains the target nucleic acid, the single-stranded nucleic acid, and reactants for nucleic acid amplification so that amplification of the target nucleic acid and detection of genetic variations initiated by cleavage of the single-stranded nucleic acid as specified above can be performed at the same time. In each amplification process, it is necessary to optimize the conditions for buffers and primers, reaction temperature, and cleavage conditions for the single-stranded nucleic acid. The use of the detection method of the present invention in conjunction with the nucleic acid amplification technologies may provide remarkably improved detection speed and sensitivity for the target nucleic acid.

On the other hand, the single-stranded nucleic acid for real-time detection of a genetic variation of a single target gene according to the present invention can ensure fast and accurate detection of the gene with cancerous point mutations such as KRAS or EGFR. Accordingly, the single-stranded nucleic acid is applicable to the cancer diagnostic kit or the cancer diagnostic composition, to provide information about the development of cancers through real-time diagnosis for cancer.

MODE FOR INVENTION

Hereinafter, the present invention will be described in further detail with reference to examples. It will be obvious to those skilled in the art that these examples are illustrative purposes only and are not intended to limit the scope of the present invention.

Example 1: Analysis of ApoE Using Type 1 Single-Stranded Nucleic Acid

A type 1 single-stranded nucleic acid was used to analyze six genotypes (E2/E2, E3/E3, E4/E4, E2/E3, E2/E4, E3/E4) of the apolipoprotein E (ApoE) gene.

In human, the ApoE gene situated on chromosome 19 is implicated in cardiovascular disease and Alzheimer disease. There are three allelic isoforms of the ApoE gene: ApoEε2, ApoEε3, and ApoEε4, which result from single nucleotide polymorphisms (SNPs) in DNA of codon 112(cys/arg) and codon 158(cys/arg) [genome DNA position 586(T/C), 724 (T/C)]. The combination of the allelic isoforms provides six genotypes (E2/E2, E3/E3, E4/E4, E2/E3, E2/E4, E3/E4) of the ApoE gene. A 4-plex analysis was enabled using four type 1 single-stranded nucleic acids, each of which was improved by labeling its 5'-end with a different fluorescent dye for discrimination of the six genotypes of the ApoE gene. The present invention presented analytical results acceptable with satisfaction in the aspects of sensitivity and specificity of the 4-plex analysis system; whereas the conventional analysis methods were far from satisfaction.

In order to measure the genetic expression of SNP mutants for ApoE genotypes of codons 112 and 158, the type 1 single-stranded nucleic acids of the present invention and the primers were constructed by IDT (Integrated DNA Technologies, USA) as shown in Table 1 below. For the type 1 single-stranded nucleic acids, acting as a probe having a structure of X—Y—Z, the 5' ends were labeled with 6-FAM™ (6-carboxyfluorescein), HEX™ (hexachloro-6-carboxyfluorescein), Texas Red™, (a mixture of isomeric sulfonyl chlorides and sulforhodamine; Invitrogen™), and Cy®5 (sulfoindodicarbocyanine dye), respectively, and the 3' ends were labeled with IABKFQ (non-fluorescent arylazo-based quencher). For ribonucleotide (RNA), the letter "r" was added to the front of the sequence for discrimination from deoxyribonucleotide (DNA).

μM), the ApoE forward primer (final concentration 0.35 μM), and the ApoE reverse primer (final concentration 0.35 μM) were prepared as shown in Table 1.

Each of the weighed genomic DNAs, 0.5 U RNase-H, 4 μl of AptaTaq DNA Master (Roche), and 3 μl of GC rich solution (Roche) were placed in a tube. The total volume was adjusted to 20 μl using nuclease-free water, and the polymerase chain reaction (PCR) was activated. The PCR reaction was performed for 45 cycles, each cycle consisting of 5 minutes at 95° C., 15 seconds at 95° C., and 70 seconds at 65° C. The results of the PCR are presented in FIG. 1.

As can be seen from the results, six combinations of the ApoE alleles could be analyzed in one reaction well. Further, the discrimination performance for mutants was highly enhanced by using the improved probe when the mutants were total or partial mutation like congenital mutations.

Example 2: Analysis of Kras Mutant Using Type 1 Single-Stranded Nucleic Acid

Example 2-1: Real-Time Analysis of Kras G13D Mutant Using Single-Stranded Nucleic Acid of the Present Invention In order to measure the genetic expression of the KRAS G13D mutant using the type 1 single-stranded nucleic acid

TABLE 1

| Primer/Probe name | Sequences | SEQ ID NO |
|---|---|---|
| ApoE-specific primer set and four ApoE single-stranded nucleic acids (type 1) | | |
| ApoE_F primer | 5'-GAAGGCCTACAAATCGGAACT-3' | 1 |
| ApoE_R primer | 5'-GCCACCTGCTCCTTCAC-3' | 2 |
| ApoE Nucleic acid 1 | 56-FAM/-GAGGACGTGrUGCGGCC-/3IABkFQ | 3 |
| ApoE Nucleic acid 2 | 5-HEX/-GAGGACGTGrCGCGGCC-/3IABkFQ | 4 |
| ApoE Nucleic acid 3 | 5-TexRd/-CTGCAGAAGrUGCCTGGCA-/3IABkFQ | 5 |
| ApoE Nucleic acid 4 | 5-Cy5/-GCAGAAGrCGCCTGGCA-/3IABkFQ | 6 |

For analysis, human cell lines, PC3(E2/E2), A549(E3/E3), and U937(E4/E4), were purchased from Korean Cell Line Bank (KCLB) and used to extract genomic DNAs. For analysis of the six genotypes, PC3(E2/E2), A549(E3/E3), and U937(E4/E4) were used for homozygous genotypes; and combinations of genomic DNAs, that is, PC3+A549 (E2/E3), PC3+U937(E2/E4), A549+U937(E3/E4), were used for heterozygous genotypes. Each genomic DNA at high concentration was weighed to an amount of 32 ng (about 10⁴ copy) per reaction.

Each of the ApoE single-stranded nucleic acids 1, 2, 3, and (final concentration 0.2 μM, 0.15 μM, 0.15 μM, 0.075 of the present invention, IDT (Integrated DNA Technologies, USA) was asked to construct the single-stranded nucleic acid (type 1) from KRAS G13D mutant cell-line, the single-stranded nucleic acid (type 1) from KRAS wild-type cell-line, and a forward primer and a reverse primer from KRAS G13D-mutant cell-line, as shown in Table 2 below. For the single-stranded nucleic acids, the 5' ends were labeled with HEX and FAM, respectively, and the 3' ends were labeled with IABkFQ. For ribonucleotide (RNA), the letter "r" was added to the front of the sequence for discrimination from deoxyribonucleotide (DNA).

TABLE 2

KRAS G13D-mutant single-stranded nucleic acid, wild-type
single-stranded nucleic acid, and primer set specific to G13D
mutant

| Primer/Probe name | Sequences | SEQ ID NO |
|---|---|---|
| G13D Nucleic acid | HEX/-AGCTGGTGrACGTAGGC-/3IABkFQ | 7 |
| Wild-type Nucleic acid | FAM/-AGCTGGTGrGCGTAGGC-/3IABkFQ | 8 |
| G13D_F primer | 5'-CCTGCTGAAAATGACTGAATATAAACT-3' | 9 |
| G13D_R primer | 5'-TCGTCCACAAAATGATTCTGAATTAG-3' | 10 |

The KRAS gene to be measured was detected from the total genomic DNAs extracted from HCT-15 cell-line and NCI-H1975 cell-line, which were incubated for a defined period of time. The total genomic DNAs were extracted from 5×10⁶ cells of each cell-line with a PureLink Genomic DNA Mini Kit (Thermo Fisher Scientific, Cat No. K1820-00) and weighed with a NanoDrop One (Thermo Fisher Scientistic). The weighed total genomic DNAs were diluted to 15 ng/μl. Then, a 1/10 serial dilution was made to prepare 2 μl of the genomic DNA with concentration of 15 ng/μl~1.5 pg/μl for each use. HCT-15 is known as G13D-mutant cell-line, and NCI-H1975 is known as KRAS wild-type cell-line.

Figure 2:
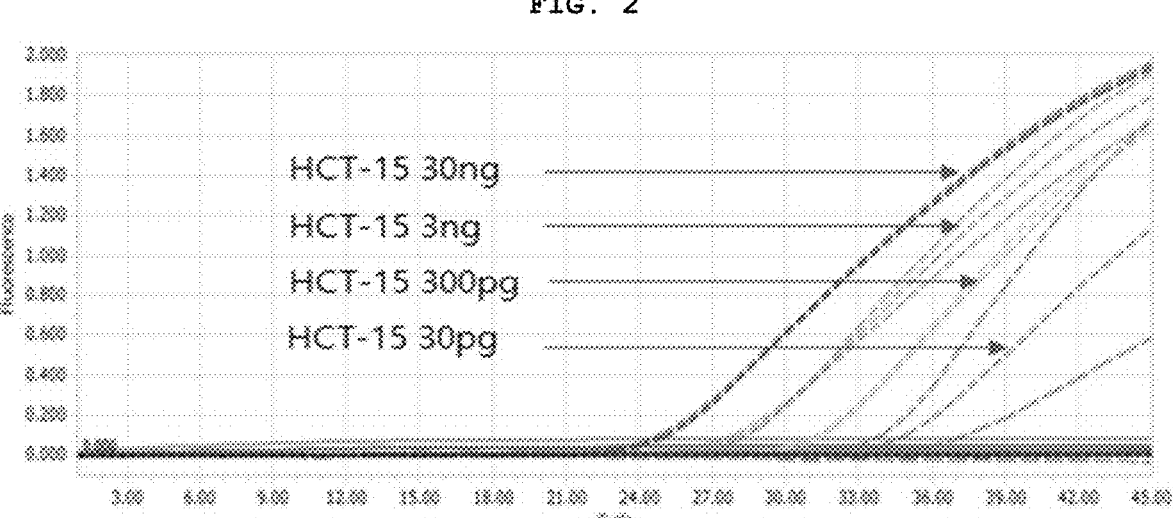
FIG. 2 is a presentation of PCR results measuring the genetic expression of KRAS G13D mutant using a single-stranded nucleic acid type 1 according to another embodiment of the present invention. Genomic DNA (gDNA) from G13D-mutant HCT-15 cell-line was diluted by concentrations, and PCR was carried out using a G13D single-

Subsequently, 0.3 μl of G13D single-stranded nucleic acid (10 μM, SEQ ID NO: 7) and 0.5 μl of each primer (10 μM, SEQ ID NO: 9, 10) were constructed. In the presence of the single-stranded nucleic acid and the primers, each of the total genomic DNAs from HCT-15 cell-line (30 ng, 3 ng, 300 pg, 30 pg) was added to 0.5 U RNase-H, 4 μl of AptaTaq DNA Master (Roche), the total genomic DNA from NCI-H1975 cell-line (30 ng). The total volume was adjusted to 20 μl using deionized water, and the polymerase chain reaction (PCR) was performed to measure the G13D mutant. In this regard, the PCR reaction was performed for 40 cycles, each cycle consisting of 10 minutes at 95° C. (initial denaturation), 10 seconds at 95° C., and 60 seconds at 64° C. The real-time measurements of signal HEX were acquired in each cycle. The measurement results are presented in FIG. 2.

Example 2-2: Real-Time Analysis of Kras
Wild-Type Mutant Using Single-Stranded Nucleic
Acid of the Present Invention Under the same conditions of Example 2-1, in the presence of the KRAS wild-type single-stranded nucleic acid (SEQ ID NO: 8) and the primers (SEQ ID NO: 9, 10), each of the total genomic DNAs from NCI-H1975 cell-line (30 ng, 3 ng, 300 pg, 30 pg) and each of the total genomic DNAs from HCT-15 cell-line (30 ng, 3 ng, 300 pg, 30 pg) were placed in a tube. The KRAS wild-type gene was then measured. The measurement results are presented in FIG. 3. The HCT-15 cell-line is a heterozygous type gene and contains both the G13D mutant gene (Refer to the results of FIG. 2) and the KRAS wild-type gene. The same results of FIG. 4 were acquired even when the HCT-15 cell-line had no more than half the wild-type gene.

Example 2-3: Real-Time Analysis of G13D Mutant
Mixed with Kras Wild-Type Gene Using
Single-Stranded Nucleic Acid of the Present
Invention The KRAS gene to be measured was detected from the total genomic DNA extracted from the HCT-15 cell-line and the NCI-H1975 cell-line that were incubated for a defined period of time. The total genomic DNA was extracted from 5×10⁶ cells of each cell-line with a PureLink Genomic DNA Mini Kit (Thermo Fisher Scientific, Cat No. K1820-00) and weighed with a NanoDrop One (Thermo Fisher Scientistic). The weighed NCI-H1975 DNA was diluted to 30 ng/μl, and the HCT-15 DNA was diluted to 30 ng/μl. Then, a 1/10 serial dilution was made to prepare the NCI-H1975 genomic DNA and the HCT-15 genomic DNA with concentration of 3 ng/μl~3 pg/μl. 2 μl of the NCI-H1975 genomic DNA and 2 μl of the HCT-15 genomic DNA were combined together so that the concentration of the HCT-15 was 10 to 0.01% with respect to the concentration of the NCI-H1975. HCT-15 is known as G13D-mutant cell-line, and NCI-H1975 is known as KRAS wild-type cell-line.

Subsequently, 0.3 μl of G13D single-stranded nucleic acid (10 μM, SEQ ID NO: 7) and 0.5 μl of each primer (10 μM, SEQ ID NO: 9, 10) were constructed. In the presence of the single-stranded nucleic acid and the primers, 0.5 U RNase-H, 4 μl of AptaTaq DNA Master (Roche), and DNA diluted to 10 to 0.01% were added in a tube. The total volume was adjusted to 20 μl using deionized water, and the polymerase chain reaction (PCR) was performed to measure the G13D mutant. In this regard, the PCR reaction was performed for 40 cycles, each cycle consisting of 10 minutes at 95° C. (initial denaturation), 10 seconds at 95° C., and 60 seconds at 64° C. The real-time measurements of signal HEX were acquired in each cycle. The measurement results are presented in FIG. 5.

As can be seen from FIGS. 2 to 5, using the G13D single-stranded nucleic acid (type 1) in detection of G13D mutant caused no cross-reaction with the NCI-H1975 wild-type genomic DNA, providing high specificity, but low detection when using 600 pg or less of the HCT-15 genomic DNA. This implicitly showed that there was a problem with the detection when wild-type genes were mixed with the genes harboring point mutation, particularly in the case that the genes with point mutation took up less than 10%.

Example 3: Analysis of ApoE Using Type 2
Single-Stranded Nucleic Acid

The type 2 single-stranded nucleic acids of the present invention were employed to measure the genetic expression of SNP mutants for ApoE genotypes of codons 112 and 158. The IDT (Integrated DNA Technologies, USA) was asked to construct the type 2 single-stranded nucleic acids as shown in Table 3 below.

For the type 2 single-stranded nucleic acids, acting as a primer and a probe having a structure of X-Y-Z, the 5' ends were labeled with FAM, HEX, and TexasRed, and Cy5, respectively, and the 3' ends were labeled with IABkFQ. For ribonucleotide (RNA), the letter "r" was added to the front of the sequence for discrimination from deoxyribonucle-otide (DNA).

stranded nucleic acids of the present invention, there was a limitation that the 586T mutant at codon 112 and the 724T mutant at codon 158 were discriminable from each other not by the fluorescent dye but by the fluorescence intensity at the end point because a same fluorescence dye was used. This could be a problem with the interpretation of the analytical results based on the concentration of the DNA sample. In conclusion, using the type 1 single-stranded nucleic acids as shown in Example 1 was more beneficial to the better analysis of the congenital mutant, ApoE, than using the type 2 single-stranded nucleic acids.

TABLE 3

| Four ApoE single-stranded nucleic acids (type 2) | | |
|---|---|---|
| Nucleic acid name | Sequences | SEQ ID NO |
| ApoE Nucleic acid 1 | 56-FAM/-CGGTCATGGAGGACGTGrUGC-/3IABkFQ | 11 |
| ApoE Nucleic acid 2 | 5TexRd-XN/-GCGGATATGGAGGACGTrGCG-/3IABkFQ | 12 |
| ApoE Nucleic acid 3 | 56-FAM/-CTGGTACACTGCCAGGCArCTT-/3IABkFQ | 13 |
| ApoE Nucleic acid 4 | 5HEX/-CTGGTACACTGCCAGGCrGATTC-/3IABkFQ | 14 |

For analysis, human cell lines, PC3(E2/E2), A549(E3/E3), and U937(E4/E4), were purchased from Korean Cell Line Bank (KCLB) and used to extract genomic DNAs. For analysis of six genotypes, PC3(E2/E2), A549(E3/E3), and U937(E4/E4) were used for homozygous genotypes; and combinations of genomic DNAs, that is, PC3+A549(E2/E3), PC3+U937(E2/E4), A549+U937(E3/E4), were used for het-erozygous genotypes. Each genomic DNA at high concentration was weighed to an amount of 32 ng (about $10^4$ copy) per reaction.

In the presence of the ApoE single-stranded nucleic acids 1, 2, 3, and 4 (final concentration 0.375 μM, 0.1 μM, 0.25 μM, and 0.25 μM) shown in Table 3, the weighed genomic DNA, 0.1 ng of heat-resistant RNase H, 4 μl of AptaTaq DNA Master w/o MgCl₂ (Roche), 4 μl of GC rich solution (Roche), 2.75 mM MgCl₂, and 62.5 nM Low ROX were placed in a tube. The total volume was adjusted with nuclease-free water to 20 μl, and the polymerase chain reaction (PCR) was activated. The PCR reaction was per-formed for 40 cycles, each cycle consisting of 10 minutes at 95° C., 15 seconds at 95° C., and 55 seconds at 64° C. The results of the PCR are presented in FIG. 6.

As can be seen from the results, in the analysis for the six combinations of the ApoE alleles using the type 2 single- Example 4: Analysis of Kras Mutant Using Type 2 Single-Stranded Nucleic Acid Example 4-1: Real-Time Analysis of G12V, G12C and G12S Mutants Using Type 2 Single-Stranded Nucleic Acid of the Present Invention The type 2 single-stranded nucleic acids were used to measure the genetic expression of three G13D/G12C/G12S mutants in KRAS codon 12. IDT (Integrated DNA Tech-nologies, USA) was asked to construct the single-stranded nucleic acids of the present invention and the Uni-reverse primer, as shown in Table 4 below. For the single-stranded nucleic acids, the 5' ends were labeled with HEX, FAM and Cy5, respectively, and the 3' ends were labeled with IABkFQ. For ribonucleotide (RNA), the letter "r" was added to the front of the sequence for discrimination from deoxy-ribonucleotide (DNA).

TABLE 4

| Single-stranded nucleic acids and primer used in analysis of KRAS mutants | | |
|---|---|---|
| Nucleic acid/ Primer name | Sequences | SEQ ID NO |
| G12V Nucleic acid | HEX/-ACTTGTGGTAGTTGGAGCTGrUTG-/3IABkFQ | 15 |
| G12C Nucleic acid | Cy5/-AACTTGTGGTAGTTGGAGCTrUGT-/3IABkFQ | 16 |
| G12S Nucleic acid | FAM/-AACTTGTGGTAGTTGGAGCTrAGT-/3IABkFQ | 17 |

TABLE 4-continued

| Single-stranded nucleic acids and primer used in analysis of KRAS mutants | | |
|---|---|---|
| Nucleic acid/ Primer name | Sequences | SEQ ID NO |
| Uni-reverse primer | 5'-CATATTCGTCCACAAAATGATTCTG-3' | 18 |

In order to determine the detection performance for KRAS point mutation using the synthesized single-stranded nucleic acids, the wild-type cell-line and the mutant cell-line were incubated, and the total genomic DNA was extracted from $5 \times 10^6$ cells of each cell-line with a PureLink Genomic DNA Mini Kit (Thermo Fisher Scientific, Cat No. K1820-00). Meanwhile, the total genomic DNA was weighed with a NanoDrop One (Thermo Fisher Scientistic) and used as a template. The cell-lines as used herein are as shown in Table 5 below.

TABLE 5

| Cell-lines for three G13D/G12C/G12S mutants in KRAS codon 12 | | |
|---|---|---|
| Mutant cell-line | Cell-line names | Type |
| G12V mutant cell-line | SW620 | Homozygous |
| G12C mutant cell-line | MIA-Paca2 | Homozygous |
| G12S mutant cell-line | A549 | Homozygous |

Subsequently, 0.5 µl of the G12V single-stranded nucleic acid (10 µM, SEQ ID NO: 15) and 0.5 µl of the primer (10 µM, SEQ ID NO: 18) were prepared. In the presence of the single-stranded nucleic acid and the primer, the total genomic DNA from Colo201 (KRAS wild-type cell-line) (30 ng) and each of the total genomic DNA from SW620 (G12V mutant) cell-line (3 ng, 300 pg, 30 pg, 3 pg) were added to 3.6 µl of 5×AptaTaq DNA Master (Roche) and 0.2 µl of heat-resistant RNase H. The total volume was adjusted to 20 µl using deionized water, and the polymerase chain reaction (PCR) was performed to measure the G12V mutant. The PCR reaction included a first PCR reaction performed for 4 cycles, each cycle consisting of 10 minutes at 95° C. (initial denaturation), 15 seconds at 95° C., and 30 seconds at 66° C.; and a second PCR reaction performed for 40 cycles, each cycle consisting of 15 seconds at 85° C. and 40 seconds at 64° C. The real-time measurements of signal HEX were acquired in each cycle. The measurement results are presented in FIG. 7.

In addition, 0.5 µl of the G12C single-stranded nucleic acid (10 µM, SEQ ID NO: 16) and 0.5 µl of the primer (10 µM, SEQ ID NO: 18) were prepared. In the presence of the single-stranded nucleic acid and the primer, the total genomic DNA from Colo201 (KRAS wild-type cell-line) (70 ng) and each of the total genomic DNAs from MIA-Paca2 (G12C mutant) cell-line (7 ng, 700 pg, 70 pg, 7 pg) were added to 2.8 µl of 5×AptaTaq DNA Master (Roche), 1.2 µl of 5× Apta Fast buffer, 0.4 µl of heat-resistant RNase H (1 U/µl), and 0.5 µl of 25 mM MgCl₂. The total volume was adjusted to 20 µl using deionized water, and the polymerase chain reaction (PCR) was carried out to measure the G12C mutant. The PCR reaction was performed for 40 cycles, each cycle consisting of 10 minutes at 95° C. (initial denaturation), 10 seconds at 95° C., and 60 seconds at 64°

C. The real-time measurements of signal Cy5 were acquired in each cycle. The measurement results are presented in FIG. 8.

In addition, 0.5 µl of the G12S single-stranded nucleic acid (10 µM, SEQ ID NO: 17) and 0.5 µl of the primer (10 µM, SEQ ID NO: 18) were prepared. In the presence of the single-stranded nucleic acid and the primer, the total genomic DNA from Colo201 (KRAS wild-type cell-line) (30 ng) and each of the total genomic DNAs from A549 (G12S mutant) cell-line (3 ng, 300 pg, 30 pg, 7 pg) were added to 3.6 µl of 5×AptaTaq DNA Master (Roche) and 0.2 µl of heat-resistant RNase H (10 ng/µl). The total volume was adjusted to 20 µl using deionized water, and the polymerase chain reaction (PCR) was carried out to measure the G12S mutant. The PCR reaction was performed for 40 cycles, each cycle consisting of 10 minutes at 95° C. (initial denaturation), 10 seconds at 95° C., and 60 seconds at 64° C. The real-time measurements of signal FAM were acquired in each cycle. The measurement results are presented in FIG. 9.

As can be seen from FIGS. 7, 8 and 9, using the single-stranded nucleic acids of the present invention made the analysis of mutants possible with high detection performance in the aspects of specificity and sensitivity even when the gene with point mutation took up less than 0.01%.

Example 5: Analysis Method for EGFR Mutant Using Type 2 Single-Stranded Nucleic Acid Epidermal growth factor receptor (EGFR) is very common with non-small cell lung cancer, and the EGFR tyrosine kinase (TKI) targets the EGFR. The drug reactions of the therapeutic drugs in patients with non-small cell lung cancer can be predicted with the analysis of the mutation occurring in the tyrosine kinase domains corresponding to the Exons 18, 19, 20, and 21 of the EGFR gene. The analysis of the related mutations is thus helpful in selecting therapeutic drugs and treating the disease. In this example, analysis was conducted to measure the expression of the most frequently used mutation, T790M(C2369T).

IDT (Integrated DNA Technologies, USA) was asked to construct the type 2 single-stranded nucleic acid of the present invention and a primer as shown in Table 6 below. For the T790M single-stranded nucleic acid, the 5' end was labeled with FAM, and the 3' end was labeled with IABkFQ. For ribonucleotide (RNA), the letter was added to the front of the sequence for discrimination from deoxyribonucleotide (DNA).

TABLE 6

Single-stranded nucleic acids and primer used in analysis
of EGFR mutant

| Nucleic acid/ Primer name | Sequences | SEQ ID NO |
|---|---|---|
| T790M Nucleic acid | 56-FAM/-CCGTGCAGCTCATCArUGC-/3IABkFQ | 19 |
| T790M primer | 5'-CCTTGTGTTAAAGGACATAGTCCAG-3' | 20 |

For analysis, genomic DNAs were extracted from the H1975 cell-line harboring T790M mutation and the wild-type A549 cell-line. 30 ng (about $1\times10^4$ copy) of the genomic DNA from H1975 and 30 ng (about $1\times10^4$ copy) of the genomic DNA from A549 were weighed and diluted 10-fold.

The T790M single-stranded nucleic acid (final concentration 0.25 μM) and the T790M primer (final concentration 0.25 μM) shown in FIG. 6 were prepared. In the presence of the single-stranded nucleic acid and the primer, the weighed genomic DNAs, 0.5 U heat-resistant RNase-H, and 3.6 μl of 5×AptaTaq DNA Master (Roche) were place in a tube. The total volume was adjusted to 20 μl using nuclease-free water, and the polymerase chain reaction (PCR) was activated. The PCR reaction was performed for 45 cycles, each cycle consisting of 10 minutes at 95° C., 15 seconds at 95° C., and 60 seconds at 64° C. The results of the PCR are presented in FIG. 10.

As can be seen from the results, 0.1% mutation analysis was possible according to the comparison between mutant gene and wild-type gene in the EGFR mutation analysis using the single-stranded nucleic acid of the present invention. This implicitly showed that using the type 2 single-stranded nucleic acid as described above was more favorable than using the type 1 single-stranded nucleic acid in the detection of acquired mutations such as cancerous point mutations.

Example 6: Analysis of Let-7 miRNA and miRNA 34 Isoforms Using Type 2 Single-Stranded Nucleic Acid Example 6-1: Real-Time Analysis of Let-7 miRNA Using Type 2 Single-Stranded Nucleic Acid of the Present Invention let-7 miRNA is known to have the most isoforms among the miRNAs. The let-7 isoforms are very hard to discriminate from each other, really difficult when the specificity is less than 1%. In order to measure the genetic expression of let-7a (5'-UGAGGUAGUAGGUUGUAUAGUU) (SEQ ID NO: 39) and let-7d (5'-AGAGGUAGUAGGUUG-CAUAGUU) (SEQ ID NO: 40) genes in this experiment, IDT (Integrated DNA Technologies, USA) was asked to construct the type 2 single-stranded nucleic acid of the present invention, the primer, and the RT-primer as shown in FIG. 7 below. For accurate quantity, the construction of let-7 miRNA was asked to IDT. For the single-stranded nucleic acids, the 5' ends were labeled with fluorescein succinimidyl ester (FAM), and the 3' ends were labeled with 3IABKFQ. For ribonucleotide (RNA), the letter "r" was added to the front of the sequence for discrimination from deoxyribonucleotide (DNA).

TABLE 7

Single-stranded nucleic acids and primers used in
discrimination of let-7 miRNA isoforms

| Nucleic acid/ Primer name | Sequences | SEQ ID NO |
|---|---|---|
| let-7a Nucleic acid | FAM/-GCTGCTTGAGGTAGTAGGTTGrUAT-/3IABkFQ | 21 |
| let-7a R primer | 5'-GCCGCTGAGGTAGTAGGT-3' | 22 |
| let-7a RT primer | 5'-GCTAACGTCTGTACTTCGTCA(TTT)nAACT-3' | 23 |
| let-7d Nucleic acid | FAM/-GCTGCTAGAGGTAGTAGGTTGrCAT-/3IABkFQ | 24 |
| let-7d R primer | 5'-GCCGCTGAGGTAGTAGGT-3' | 25 |
| let-7d RT primer | 5'-GCTAACGTCTGTACTTCGTCA(TTT)nAACT-3' | 26 |

In the presence of each RT primer of Table 7 (1 μl, 10 μM), a poly-(A) tailing kit (Ambion) and an Nxtscript RT kit (Roche) (20 μl in total) were used to synthesize cDNA from 1 μl of each miRNA (20 pM) through a reaction at 45° C. for 30 minutes.

The synthesized cDNA was diluted to a concentration of 100 fM to 1 aM.

With 0.5 μl of each single-stranded nucleic acid (10 μM) and 0.5 μl of each primer (10 μM) shown in Table 7, 2 μl of the diluted let-7a cDNA (100 fM to 1 aM, by 1/10 dilution) was added to 2 μl of let-7d cDNA (1 pM). 1 U heat-resistant RNase H and 4 μl of AptaTaq DNA Master (Roche) were further added. The total volume was adjusted to 20 μl using deionized water, and the polymerase chain reaction (PCR) was performed. In this regard, the PCR reaction was performed for 45 cycles, each cycle consisting of 5 minutes at 95° C., 60 seconds at 63 to 64° C., and 10 seconds at 95° C. The measurement results are presented in FIGS. 11 and 12.

As can be seen from the results, the analysis of each miRNA was made feasible by using no more than 2 μl (about 1 copy) of the diluted cDNA (containing 1 aM miRNA).

Example 6-2: Real-Time Specificity-Detection of Let-7 miRNA Using Type 2 Single-Stranded Nucleic Acid of the Present Invention In the presence of 0.5 μl of each single-stranded nucleic acid (10 μM) and 0.5 μl of each primer (10 μM) shown in

Example 6-3: Real-Time Analysis of miRNA 34a, miRNA 34b and miRNA 34c Using Type 2 Single-Stranded Nucleic Acid of the Present Invention miRNA 34 has three isoforms, which are considerably difficult to discriminate from one another. In order to measure the genetic expression of miRNA 34a, miRNA 34b and miRNA 34c, IDT (Integrated DNA Technologies, USA) was asked to construct the single-stranded nucleic acids, the primers, and the RT-primers as shown in FIG. 8 below. For the single-stranded nucleic acids, the 5' ends were labeled with fluorescein succinimidyl ester (FAM), and the 3' ends were labeled with 3IABkFQ. For ribonucleotide (RNA), the letter "r" was added to the front of the sequence for discrimination from deoxyribonucleotide (DNA).

TABLE 8

Single-stranded nucleic acids and primers used in analysis of miRNA 34a, miRNA 34b and miRNA 34c

| Nucleic acid/ Primer name | Sequences | SEQ ID NO |
|---|---|---|
| miRNA 34a Nucleic acid | 56FAM/-TTGGCAGTGTCTTAGCTGrGTT- /3IABkFQ | 27 |
| miRNA 34a primer | 5'-GTCTCGACGTTCTTTTTTTTTTTTAC-3' | 28 |
| miRNA 34a RT primer | 5'-GTCTCGACGTTCTTTTTTTTTTTTTAC-3' | 29 |
| miRNA 34b Nucleic acid | 5HEX/-GTCTAGGCAGTGTCATTAGCTGrATT- /3IABkFQ | 30 |
| miRNA 34b primer | 5'-GTCTCGACGTTCTTTTTTTTTTTTTC-3' | 31 |
| miRNA 34b RT primer | 5'-GTCTCGACGTTCTTTTTTTTTTTTTTC-3' | 32 |
| miRNA 34c Nucleic acid | 56FAM/-CCAGGCAGTGTAGTTAGCTGrATT- /3IABkFQ | 33 |
| miRNA 34c primer | 5'-GTCTCGACGTTCTTTTTTTTTTTTGC-3' | 34 |
| miRNA 34c RT primer | 5'-GTCTCGACGTTCTTTTTTTTTTTTTGC-3' | 35 |

Table 7, 2 μl of the diluted let-7a cDNA (100 fM to 1 aM, by 1/10 dilution) was added to 2 μl of let-7d cDNA (1 pM). 1 U heat-resistant RNase H and 4 μl of AptaTaq DNA Master (Roche) were further added. The total volume was adjusted to 20 μl using deionized water, and the polymerase chain reaction (PCR) was performed. In this regard, the PCR reaction was performed for 45 cycles, each cycle consisting of 5 minutes at 95° C., 60 seconds at 63 to 64° C., and 10 seconds at 95° C. The measurement results are presented in FIG. 13.

As can be seen from the results, the analysis was possible with stability in the concentration range from 100 fM to 1 fM in the test group which contained 2 μl of the diluted let-7a cDNA (100 fM to 1 aM, by 1/10 dilution) added to 2 μl of let-7d cDNA (1 pM). This implicitly showed that miRNA isoform was detectable with the specificity maintained while its proportion was at least 0.1%.

In the presence of each RT primer (1 μl, 10 μM), a poly-(A) tailing kit (Ambion) and an Nxtscript RT kit (Roche) (20 μl in total) were used to synthesize cDNA from each miRNA through a reaction at 40° C. for 60 minutes. The synthesized cDNA was diluted to 7 concentrations ranging from 1 pM to 1 aM (about $10^6$~$10^0$ copy) by a 1/10 dilution, and the polymerase chain reaction (PCR) was activated. For PCR, each of the synthesized cDNAs, heat-resistant RNase H, AptaTaq DNA Master (Roche), single-stranded nucleic acids, and primers were mixed together, and the total volume was adjusted to 20 μl using deionized water. Then, the PCR was performed for 45 cycles, each cycle consisting of 5 minutes at 95° C., 10 seconds at 95° C., and 1 minute at 65° C.

As can be seen from the results, miRNA 34a, miRNA 34b and miRNA 34c were all detected with normal PCR efficiency in the concentration rage from 1 pM to 10 aM (about $10^6$~$10^1$ copy).

The results are presented in FIGS. 14, 15 and 16.

Example 6-4: Real-Time Specificity-Detection of
miRNA 34A, miRNA 34b and miRNA 34c Using
Type 2 Single-Stranded Nucleic Acid of the Present
Invention As apparent from Example 6-3, using the single-stranded
nucleic acid made the isoforms of miRNA 34a, miRNA 34b
and miRNA 34c discriminable from one another. In this
example, it was intended to determine the minimum pro-
portion of a specific miRNA isoform to be amplified at
which the miRNA isoform could be discriminable from the
other miRNA isoforms while mixed with the other miRNA
isoforms. $10^8$ copy (100 pM) of miRNA 3a or miRNA 34b
isoform was mixed with miRNA 34c isoform diluted to a
concentration of $10^7$ to $10^4$ or $10^3$ copy (10 pM to 10 fM) by
a 1/10 dilution. The miRNA 34c single-stranded nucleic acid
and the primer were used to perform the specificity-detec-
tion with polymerase chain reaction (PCR). For PCR, each
of the synthesized cDNAs, heat-resistant RNase H, AptaTaq
DNA Master (Roche), single-stranded nucleic acids, and
primers were mixed together, and the total volume was
adjusted to 20 μl using deionized water. Then, the PCR was performed for 45 cycles, each cycle consisting of 5 minutes
at 95° C., 10 seconds at 95° C., and 1 minute at 65° C.

The results are presented in FIGS. 17 and 18.

As can be seen from the results, miRNA 34c was detected
with the specificity maintained while its proportion was at
least 0.001%.

Example 7: Analysis Method Depending on
Structure of Single-Stranded Nucleic Acid It was intended to increase the specificity in mutant
detection using the single-stranded nucleic acid (type 2)
according to the present invention. Specifically, to determine
the detection performance for mutant as a function of the
locus of the ribonucleotide (RNA) in the single-stranded
nucleic acid, IDT (Integrated DNA Technologies, USA) was
asked to construct three types of G12D (i.e., R1DrMR2,
R1rDMR2 and R1DMrDR2) shown in Table 9 below. For
each single-stranded nucleic acid, the 5' end was labeled
with FAM, and the 3' end was labeled with 3IABkFQ. For
ribonucleotide (RNA), the letter "r" was added to the front
of the sequence for discrimination from deoxyribonucle-
otide (DNA).

TABLE 9

Single-stranded nucleic acids for three types of KRAS G12D

| Nucleic acid name | Sequences | SEQ ID NO |
|---|---|---|
| G12D-R1DrMR2 | FAM/-CTTGTGGTAGTTGGAGCTGrATG-/3IABkFQ | 36 |
| G12D-R1rDMR2 | FAM/-CTTGTGGTAGTTGGAGCTrGAT-/3IABkFQ | 37 |
| G12D-R1DMrDR2 | FAM/-CTTGTGGTAGTTGGAGCTGArTGG-/3IABkFQ | 38 |

*R1, R2: DNAoligo, D: DNA, r: RNA, M: mutation

Example 7-1: Analysis of G12D Mutant Gene and
Kras Wild-Type Gene Depending on Type of G12D
Single-Stranded Nucleic Acid (G12D-R1DrMR2,
G12D-R1rDMR2, G12D-R1DMrDR2)

0.5 μl of each single-stranded nucleic acid (10 μM, SEQ
ID NO: 36, 37, 38) and 0.5 μl of the primer (10 μM, SEQ ID
NO: 18) were constructed. In the presence of the single-
stranded nucleic acid and the primer, 0.5 U RNase H, 3.6 μl
of AptaTaq Master (Roche), and 30 ng of total genomic
DNAs extracted from Aspc-1 (G12D mutant) and HT-29
(KRAS wild-type) were placed in a tube. The total volume
was adjusted to 20 μl using deionized water, and the poly-
merase chain reaction (PCR) was activated. The PCR reac-
tion was performed for 45 cycles, each cycle consisting of
10 minutes for initial denaturation at 95° C., 10 seconds at
95° C., and 60 seconds at 64° C. The measurement results
are presented in FIGS. 19, 20 and 21.

As can be seen from the results, the three different
structures of the single-stranded nucleic acid led to different
values of specificity to the KRAS wild-type gene; even
though, the point mutation was detectable irrespective of the
structure of the single-stranded nucleic acid.

What is claimed is:

1. A method for simultaneously and real-time detecting six (6) different genotypes of ApoE gene, the method comprising the steps of: (a) obtaining a target nucleic acid comprising ApoE gene single nucleotide polymorphism sites to be detected from a biological sample; (b) preparing labeled single-stranded nucleic acids of SEQ ID Nos: 11 to 14 acting as a primer and a probe, each single-stranded nucleic acid consisting of: (i) a RNA region; (ii) a first DNA region at the 5' side of the RNA region; and (iii) a second DNA region at the 3' side of the RNA region; (c) mixing the target nucleic acid obtained in step (a), the single-stranded nucleic acids of SEQ ID Nos: 11 to 14 prepared in step (b) and a cleavage reagent, followed by amplifying the target nucleic acid through an extension reaction, wherein the single-stranded nucleic acids of SEQ ID Nos: 11 to 14 hybridize to the target nucleic acid at specific single nucleotide polymorphism sites of the ApoE gene and the cleavage reagent specifically cleaves the first RNA region from the first DNA region in each single-stranded nucleic acid; and (d) measuring the amount of the cleaved first DNA region, thereby detecting six (6) different genotypes of the ApoE gene.

2. The method as claimed in claim 1, wherein the target nucleic acid comprising ApoE gene single nucleotide polymorphism sites in step (a) is a genomic DNA.

3. The method as claimed in claim 1, wherein the cleavage reagent of step (c) is a ribonuclease (RNase) selected from the group consisting of RNaseH, RNase II, RNase III, RNase IV and RNase T2.

\*    \*    \*    \*    \*